United States Patent [19]
Berg et al.

[11] Patent Number: 5,595,736
[45] Date of Patent: Jan. 21, 1997

[54] COMPOUNDS AND METHODS FOR TREATMENT OF THROMBOEMBOLIC DISORDERS

[75] Inventors: David T. Berg, Beech Grove; Brian W. Grinnell, Indianapolis, both of Ind.

[73] Assignee: Eli Lilly and Company, Indianapolis, Ind.

[21] Appl. No.: 411,260

[22] Filed: Mar. 27, 1995

Related U.S. Application Data

[62] Division of Ser. No. 689,410, Apr. 22, 1991, abandoned.

[51] Int. Cl.$^6$ .......................... A61K 38/46; A61K 38/49; C12N 9/48; C12N 9/64
[52] U.S. Cl. .................... 424/94.64; 424/94.63; 435/212; 435/226
[58] Field of Search .................... 424/94.63, 94.64; 435/212, 226, 172.3

[56] References Cited

U.S. PATENT DOCUMENTS 5,106,741 4/1992 Marotti .................................. 435/226

FOREIGN PATENT DOCUMENTS

| 0297066 | 12/1988 | European Pat. Off. . |
|---|---|---|
| 63-230083 | 9/1988 | Japan . |
| WO88/10119 | 12/1988 | WIPO . |
| WO89/09266 | 10/1989 | WIPO . |
| WO89/10401 | 11/1989 | WIPO . |
| WO89/11531 | 11/1989 | WIPO . |

OTHER PUBLICATIONS

Burck, et al., 1990, *J. Biological Chemistry* 265:5170–5177.
Jackson et al., 1990, *Circulation* 82(3):930–940.
Wittmer and Howard, 1990, *Biochemistry* 29:4175–4180.
Wu, et al., 1990, *J. Cardiovascular Pharmacology* 16:197–203.
Higgins and Bennett, 1990, *Annu. Rev. Pharmacol. Toxicol.* 30:91–121.
Ny,To, et al, 1954 *PNAS* 51:5355–5359.
Pennica, D. et al 1983 *Nature* 301:214–221.

*Primary Examiner*—Dian C. Jacobson
*Attorney, Agent, or Firm*—Ronald S. Maciak

[57] ABSTRACT

The present invention provides derivatives of tissue plasminogen activator that lack the Finger, Growth Factor and Kringle 1 domains and comprise a Kringle 2 domain that is monoglycosylated at a site other than that of t-PA. Using recombinant DNA techniques, an alternate glycosylation sequence is provided within the Kringle 2 domain of these t-PA derivatives. This alternate glycosylation consensus sequence, as well as the glycosylation consensus sequence within the Serine Protease domain, is glycosylated upon the expression and secretion of these molecules from eucaryotic host cells. Thus, a homogeneous population of diglycosylated t-PA derivatives that lack the Finger, Growth Factor and Kringle 1 domains is produced.

8 Claims, 16 Drawing Sheets

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
        ( A ) LENGTH:1065 base pairs
        ( B ) TYPE:Nucleic acid
        ( C ) STRANDEDNESS:Double
        ( D ) TOPOLOGY:Linear ( i i ) MOLECULE TYPE:DNA ( x i ) SEQUENCE DESCRIPTION: SEQ ID NO:1:

```
TCT TAC CAA GGA AAC AGT GAC TGC TAC TTT GGG AAT GGG TCA        42

GCC TAC CGT GGC ACG CAC AGC CTC ACC GAG TCG GGT GCC TCC        84

TGC CTC CCG TGG AAT TCC ATG ATC CTG ATA GGC AAG GTT TAC       126

ACA GCA CAG AAC CCC AGT GCC CAG GCA CTG GGC CTG GGC AAA       168
```

| | |
|---|---:|
| CAT AAT TAC TGC CGG AAT CCT GAT GGG GAT GCC AAG CCC TGG | 210 |
| TGC CAC GTG CTG AAG AAC CGC AGG CTG ACG TGG GAG TAC TGT | 252 |
| GAT GTG CCC TCC TGC TCC ACC TGC GGC CTG AGA CAG TAC AGC | 294 |
| CAG CCT CAG TTT CGC ATC AAA GGA GGG CTC TTC GCC GAC ATC | 336 |
| GCC TCC CAC CCC TGG CAG GCT GCC ATC TTT GCC AAG CAC AGG | 378 |
| AGG TCG CCC GGA GAG CGG TTC CTG TGC GGG GGC ATA CTC ATC | 420 |
| AGC TCC TGC TGG ATT CTC TCT GCC GCC CAC TGC TTC CAG GAG | 462 |
| AGG TTT CCG CCC CAC CAC CTG ACG GTG ATC TTG GGC AGA ACA | 504 |
| TAC CGG GTG GTC CCT GGC GAG GAG GAG CAG AAA TTT GAA GTC | 546 |
| GAA AAA TAC ATT GTC CAT AAG GAA TTC GAT GAT GAC ACT TAC | 588 |
| GAC AAT GAC ATT GCG CTG CTG CAG CTG AAA TCG GAT TCG TCC | 630 |
| CGC TGT GCC CAG GAG AGC AGC GTG GTC CGC ACT GTG TGC CTT | 672 |
| CCC CCG GCG GAC CTG CAG CTG CCG GAC TGG ACG GAG TGT GAG | 714 |
| CTC TCC GGC TAC GGC AAG CAT GAG GCC TTG TCT CCT TTC TAT | 756 |
| TCG GAG CGG CTG AAG GAG GCT CAT GTC AGA CTG TAC CCA TCC | 798 |
| AGC CGC TGC ACA TCA CAA CAT TTA CTT AAC AGA ACA GTC ACC | 840 |
| GAC AAC ATG CTG TGT GCT GGA GAC ACT CGG AGC GGC GGG CCC | 882 |
| CAG GCA AAC TTG CAC GAC GCC TGC CAG GGC GAT TCG GGA GGC | 924 |
| CCC CTG GTG TGT CTG AAC GAT GGC CGC ATG ACT TTG GTG GGC | 966 |
| ATC ATC AGC TGG GGC CTG GGC TGT GGA CAG AAG GAT GTC CCG | 1008 |
| GGT GTG TAC ACC AAG GTT ACC AAC TAC CTA GAC TGG ATT CGT | 1050 |
| GAC AAC ATG CGA CCG | 1065 |

(2) INFORMATION FOR SEQ ID NO:2:

(i) SEQUENCE CHARACTERISTICS:
        (A) LENGTH:355 amino acids
        (B) TYPE:amino acid
        (D) TOPOLOGY:linear (ii) MOLECULE TYPE:protein (xi) SEQUENCE DESCRIPTION: SEQ ID NO:2:

```
Ser  Tyr  Gln  Gly  Asn  Ser  Asp  Cys  Tyr  Phe  Gly  Asn  Gly  Ser  Ala  Tyr
 1              5                       10                      15

Arg  Gly  Thr  His  Ser  Leu  Thr  Glu  Ser  Gly  Ala  Ser  Cys  Leu  Pro  Trp
              20                      25                      30

Asn  Ser  Met  Ile  Leu  Ile  Gly  Lys  Val  Tyr  Thr  Ala  Gln  Asn  Pro  Ser
              35                      40                      45

Ala  Gln  Ala  Leu  Gly  Leu  Gly  Lys  His  Asn  Tyr  Cys  Arg  Asn  Pro  Asp
          50                      55                      60

Gly  Asp  Ala  Lys  Pro  Trp  Cys  His  Val  Leu  Lys  Asn  Arg  Arg  Leu  Thr
 65                      70                      75                      80

Trp  Glu  Tyr  Cys  Asp  Val  Pro  Ser  Cys  Ser  Thr  Cys  Gly  Leu  Arg  Gln
                      85                      90                      95

Tyr  Ser  Gln  Pro  Gln  Phe  Arg  Ile  Lys  Gly  Gly  Leu  Phe  Ala  Asp  Ile
                 100                     105                     110

Ala  Ser  His  Pro  Trp  Gln  Ala  Ala  Ile  Phe  Ala  Lys  His  Arg  Arg  Ser
                 115                     120                     125
```

```
Pro  Gly  Glu  Arg  Phe  Leu  Cys  Gly  Gly  Ile  Leu  Ile  Ser  Ser  Cys  Trp
     130                 135                      140

Ile  Leu  Ser  Ala  Ala  His  Cys  Phe  Gln  Glu  Arg  Phe  Pro  Pro  His  His
145                      150                 155                           160

Leu  Thr  Val  Ile  Leu  Gly  Arg  Thr  Tyr  Arg  Val  Val  Pro  Gly  Glu  Glu
                    165                      170                      175

Glu  Gln  Lys  Phe  Glu  Val  Glu  Lys  Tyr  Ile  Val  His  Lys  Glu  Phe  Asp
               180                      185                      190

Asp  Asp  Thr  Tyr  Asp  Asn  Asp  Ile  Ala  Leu  Leu  Gln  Leu  Lys  Ser  Asp
          195                      200                 205

Ser  Ser  Arg  Cys  Ala  Gln  Glu  Ser  Ser  Val  Val  Arg  Thr  Val  Cys  Leu
     210                 215                      220

Pro  Pro  Ala  Asp  Leu  Gln  Leu  Pro  Asp  Trp  Thr  Glu  Cys  Glu  Leu  Ser
225                      230                 235                           240

Gly  Tyr  Gly  Lys  His  Glu  Ala  Leu  Ser  Pro  Phe  Tyr  Ser  Glu  Arg  Leu
               245                      250                      255

Lys  Glu  Ala  His  Val  Arg  Leu  Tyr  Pro  Ser  Ser  Arg  Cys  Thr  Ser  Gln
               260                      265                      270

His  Leu  Leu  Asn  Arg  Thr  Val  Thr  Asp  Asn  Met  Leu  Cys  Ala  Gly  Asp
          275                      280                 285

Thr  Arg  Ser  Gly  Gly  Pro  Gln  Ala  Asn  Leu  His  Asp  Ala  Cys  Gln  Gly
     290                 295                      300

Asp  Ser  Gly  Gly  Pro  Leu  Val  Cys  Leu  Asn  Asp  Gly  Arg  Met  Thr  Leu
305                      310                 315                           320

Val  Gly  Ile  Ile  Ser  Trp  Gly  Leu  Gly  Cys  Gly  Gln  Lys  Asp  Val  Pro
                    325                      330                      335

Gly  Val  Tyr  Thr  Lys  Val  Thr  Asn  Tyr  Leu  Asp  Trp  Ile  Arg  Asp  Asn
               340                      345                      350

Met  Arg  Pro
          355
```

( 2 ) INFORMATION FOR SEQ ID NO:3:

( i ) SEQUENCE CHARACTERISTICS:
        ( A ) LENGTH:1068 base pairs
        ( B ) TYPE:nucleic acid
        ( C ) STRANDEDNESS:double
        ( D ) TOPOLOGY:linear ( i i ) MOLECULE TYPE:DNA ( x i ) SEQUENCE DESCRIPTION: SEQ ID NO:3 :

```
TCT  TAC  CAA  GGA  AAC  AGT  GAC  TGC  TAC  TTT  GGC  CAG  GGG  TCA            42

GCC  TAC  CGT  GGC  ACG  CAC  AGC  CTC  ACC  GAG  TCG  GGT  GCC  TCC            84

TGC  CTC  CCA  TGG  AAT  GGG  TCC  ATG  ATC  CTG  ATA  GGC  AAG  GTT           126

TAC  ACA  GCA  CAG  AAC  CCC  AGT  GCC  CAG  GCA  CTG  GGC  CTG  GGC           168

AAA  CAT  AAT  TAC  TGC  CGG  AAT  CCT  GAT  GGG  GAT  GCC  AAG  CCC           210

TGG  TGC  CAC  GTG  CTG  AAG  AAC  CGC  AGG  CTG  ACG  TGG  GAG  TAC           252

TGT  GAT  GTG  CCC  TCC  TGC  TCC  ACC  TGC  GGC  CTG  AGA  CAG  TAC           294

AGC  CAG  CCT  CAG  TTT  CGC  ATC  AAA  GGA  GGG  CTC  TTC  GCC  GAC           336

ATC  GCC  TCC  CAC  CCC  TGG  CAG  GCT  GCC  ATC  TTT  GCC  AAG  CAC           378

AGG  AGG  TCG  CCC  GGA  GAG  CGG  TTC  CTG  TGC  GGG  GGC  ATA  CTC           420

ATC  AGC  TCC  TGC  TGG  ATT  CTC  TCT  GCC  GCC  CAC  TGC  TTC  CAG           462
```

```
GAG AGG TTT CCG CCC CAC CAC CTG ACG GTG ATC TTG GGC AGA                504

ACA TAC CGG GTG GTC CCT GGC GAG GAG GAG CAG AAA TTT GAA                546

GTC GAA AAA TAC ATT GTC CAT AAG GAA TTC GAT GAT GAC ACT                588

TAC GAC AAT GAC ATT GCG CTG CTG CAG CTG AAA TCG GAT TCG                630

TCC CGC TGT GCC CAG GAG AGC AGC GTG GTC CGC ACT GTG TGC                672

CTT CCC CCG GCG GAC CTG CAG CTG CCG GAC TGG ACG GAG TGT                714

GAG CTC TCC GGC TAC GGC AAG CAT GAG GCC TTG TCT CCT TTC                756

TAT TCG GAG CGG CTG AAG GAG GCT CAT GTC AGA CTG TAC CCA                798

TCC AGC CGC TGC ACA TCA CAA CAT TTA CTT AAC AGA ACA GTC                840

ACC GAC AAC ATG CTG TGT GCT GGA GAC ACT CGG AGC GGC GGG                882

CCC CAG GCA AAC TTG CAC GAC GCC TGC CAG GGC GAT TCG GGA                924

GGC CCC CTG GTG TGT CTG AAC GAT GGC CGC ATG ACT TTG GTG                966

GGC ATC ATC AGC TGG GGC CTG GCT TGT GGA CAG AAG GAT GTC               1008

CCG GGT GTG TAC ACC AAG GTT ACC AAC TAC CTA GAC TGG ATT               1050

CGT GAC AAC ATG CGA CCG                                                1068
```

(2) INFORMATION FOR SEQ ID NO:4:

(i) SEQUENCE CHARACTERISTICS:
        (A) LENGTH:356 amino acids
        (B) TYPE:amino acid
        (D) TOPOLOGY:linear (ii) MOLECULE TYPE:protein (xi) SEQUENCE DESCRIPTION: SEQ ID NO:4:

```
Ser Tyr Gln Gly Asn Ser Asp Cys Tyr Phe Gly Gln Gly Ser Ala Tyr
 1               5                  10                  15

Arg Gly Thr His Ser Leu Thr Glu Ser Gly Ala Ser Cys Leu Pro Trp
                20                  25                  30

Asn Gly Ser Met Ile Leu Ile Gly Lys Val Tyr Thr Ala Gln Asn Pro
            35                  40                  45

Ser Ala Gln Ala Leu Gly Leu Gly Lys His Asn Tyr Cys Arg Asn Pro
        50                  55                  60

Asp Gly Asp Ala Lys Pro Trp Cys His Val Leu Lys Asn Arg Arg Leu
65                  70                  75                  80

Thr Trp Glu Tyr Cys Asp Val Pro Ser Cys Ser Thr Cys Gly Leu Arg
                85                  90                  95

Gln Tyr Ser Gln Pro Gln Phe Arg Ile Lys Gly Gly Leu Phe Ala Asp
                100                 105                 110

Ile Ala Ser His Pro Trp Gln Ala Ala Ile Phe Ala Lys His Arg Arg
            115                 120                 125

Ser Pro Gly Glu Arg Phe Leu Cys Gly Gly Ile Leu Ile Ser Ser Cys
        130                 135                 140

Trp Ile Leu Ser Ala Ala His Cys Phe Gln Glu Arg Phe Pro Pro His
145                 150                 155                 160

His Leu Thr Val Ile Leu Gly Arg Thr Tyr Arg Val Val Pro Gly Glu
                165                 170                 175

Glu Glu Gln Lys Phe Glu Val Glu Lys Tyr Ile Val His Lys Glu Phe
                180                 185                 190

Asp Asp Asp Thr Tyr Asp Asn Asp Ile Ala Leu Leu Gln Leu Lys Ser
```

|     |     |     |     |     |     |     | 195 |     |     |     |     | 200 |     |     |     |     | 205 |     |     |
| --- | --- | --- | --- | --- | --- | --- | --- | --- | --- | --- | --- | --- | --- | --- | --- | --- | --- | --- | --- |

Asp Ser Ser Arg Cys Ala Gln Glu Ser Ser Val Val Arg Thr Val Cys
        210                     215                         220

Leu Pro Pro Ala Asp Leu Gln Leu Pro Asp Trp Thr Glu Cys Glu Leu
225                         230                     235                         240

Ser Gly Tyr Gly Lys His Glu Ala Leu Ser Pro Phe Tyr Ser Glu Arg
                    245                     250                     255

Leu Lys Glu Ala His Val Arg Leu Tyr Pro Ser Ser Arg Cys Thr Ser
                260                     265                     270

Gln His Leu Leu Asn Arg Thr Val Thr Asp Asn Met Leu Cys Ala Gly
        275                     280                     285

Asp Thr Arg Ser Gly Gly Pro Gln Ala Asn Leu His Asp Ala Cys Gln
    290                     295                     300

Gly Asp Ser Gly Gly Pro Leu Val Cys Leu Asn Asp Gly Arg Met Thr
305                     310                     315                     320

Leu Val Gly Ile Ile Ser Trp Gly Leu Gly Cys Gly Gln Lys Asp Val
                325                     330                     335

Pro Gly Val Tyr Thr Lys Val Thr Asn Tyr Leu Asp Trp Ile Arg Asp
                340                     345                     350

Asn Met Arg Pro
            355

( 2 ) INFORMATION FOR SEQ ID NO:5:

( i ) SEQUENCE CHARACTERISTICS:
        ( A ) LENGTH:1065 base pairs
        ( B ) TYPE:nucleic acid
        ( C ) STRANDEDNESS:double
        ( D ) TOPOLOGY:linear ( i i ) MOLECULE TYPE:DNA ( x i ) SEQUENCE DESCRIPTION: SEQ ID NO:5:

| | | | | | | | | | | | | | |
|---|---|---|---|---|---|---|---|---|---|---|---|---|---|
| TCT | TAC | CAA | GGA | AAC | AGT | GAC | TGC | TAC | TTT | GGC | CAG | GGG | TCA | 42 |
| GCC | TAC | CGT | GGC | ACG | CAC | AGC | CTC | ACC | GAG | TCG | GGT | GCC | TCC | 84 |
| TGC | CTC | CCG | TGG | AAT | TCC | ATG | ATC | CTG | ATA | GGC | AAG | GTT | TAC | 126 |
| ACA | GCA | CAG | AAC | GGC | AGT | GCC | CAG | GCA | CTG | GGC | CTG | GGC | AAA | 168 |
| CAT | AAT | TAC | TGC | CGG | AAT | CCT | GAT | GGG | GAT | GCC | AAG | CCC | TGG | 210 |
| TGC | CAC | GTG | CTG | AAG | AAC | CGC | AGG | CTG | ACG | TGG | GAG | TAC | TGT | 252 |
| GAT | GTG | CCC | TCC | TGC | TCC | ACC | TGC | GGC | CTG | AGA | CAG | TAC | AGC | 294 |
| CAG | CCT | CAG | TTT | CGC | ATC | AAA | GGA | GGG | CTC | TTC | GCC | GAC | ATC | 336 |
| GCC | TCC | CAC | CCC | TGG | CAG | GCT | GCC | ATC | TTT | GCC | AAG | CAC | AGG | 378 |
| AGG | TCG | CCC | GGA | GAG | CGG | TTC | CTG | TGC | GGG | GGC | ATA | CTC | ATC | 420 |
| AGC | TCC | TGC | TGG | ATT | CTC | TCT | GCC | GCC | CAC | TGC | TTC | CAG | GAG | 462 |
| AGG | TTT | CCG | CCC | CAC | CAC | CTG | ACG | GTG | ATC | TTG | GGC | AGA | ACA | 504 |
| TAC | CGG | GTG | GTC | CCT | GGC | GAG | GAG | GAG | CAG | AAA | TTT | GAA | GTC | 546 |
| GAA | AAA | TAC | ATT | GTC | CAT | AAG | GAA | TTC | GAT | GAT | GAC | ACT | TAC | 588 |
| GAC | AAT | GAC | ATT | GCG | CTG | CTG | CAG | CTG | AAA | TCG | GAT | TCG | TCC | 630 |
| CGC | TGT | GCC | CAG | GAG | AGC | AGC | GTG | GTC | CGC | ACT | GTG | TGC | CTT | 672 |
| CCC | CCG | GCG | GAC | CTG | CAG | CTG | CCG | GAC | TGG | ACG | GAG | TGT | GAG | 714 |
| CTC | TCC | GGC | TAC | GGC | AAG | CAT | GAG | GCC | TTG | TCT | CCT | TTC | TAT | 756 |

| | | | | | | | | | | | | |
|---|---|---|---|---|---|---|---|---|---|---|---|---|
| TCG | GAG | CGG | CTG | AAG | GAG | GCT | CAT | GTC | AGA | CTG | TAC | CCA | TCC | 798 |
| AGC | CGC | TGC | ACA | TCA | CAA | CAT | TTA | CTT | AAC | AGA | ACA | GTC | ACC | 840 |
| GAC | AAC | ATG | CTG | TGT | GCT | GGA | GAC | ACT | CGG | AGC | GGC | GGG | CCC | 882 |
| CAG | GCA | AAC | TTG | CAC | GAC | GCC | TGC | CAG | GGC | GAT | TCG | GGA | GGC | 924 |
| CCC | CTG | GTG | TGT | CTG | AAC | GAT | GGC | CGC | ATG | ACT | TTG | GTG | GGC | 966 |
| ATC | ATC | AGC | TGG | GGC | CTG | GGC | TGT | GGA | CAG | AAG | GAT | GTC | CCG | 1008 |
| GGT | GTG | TAC | ACC | AAG | GTT | ACC | AAC | TAC | CTA | GAC | TGG | ATT | CGT | 1050 |
| GAC | AAC | ATG | CGA | CCG | | | | | | | | | | 1065 |

( 2 ) INFORMATION FOR SEQ ID NO:6:

( i ) SEQUENCE CHARACTERISTICS:
( A ) LENGTH:355 amino acids
( B ) TYPE:amino acid
( D ) TOPOLOGY:linear ( i i ) MOLECULE TYPE:protein ( x i ) SEQUENCE DESCRIPTION: SEQ ID NO:6:

| Ser | Tyr | Gln | Gly | Asn | Ser | Asp | Cys | Tyr | Phe | Gly | Gln | Gly | Ser | Ala | Tyr |
|---|---|---|---|---|---|---|---|---|---|---|---|---|---|---|---|
| 1 | | | | 5 | | | | | 10 | | | | | 15 | |
| Arg | Gly | Thr | His | Ser | Leu | Thr | Glu | Ser | Gly | Ala | Ser | Cys | Leu | Pro | Trp |
| | | | 20 | | | | | 25 | | | | | 30 | | |
| Asn | Ser | Met | Ile | Leu | Ile | Gly | Lys | Val | Tyr | Thr | Ala | Gln | Asn | Gly | Ser |
| | | | 35 | | | | 40 | | | | | 45 | | | |
| Ala | Gln | Ala | Leu | Gly | Leu | Gly | Lys | His | Asn | Tyr | Cys | Arg | Asn | Pro | Asp |
| | 50 | | | | | 55 | | | | | 60 | | | | |
| Gly | Asp | Ala | Lys | Pro | Trp | Cys | His | Val | Leu | Lys | Asn | Arg | Arg | Leu | Thr |
| 65 | | | | | 70 | | | | | 75 | | | | | 80 |
| Trp | Glu | Tyr | Cys | Asp | Val | Pro | Ser | Cys | Ser | Thr | Cys | Gly | Leu | Arg | Gln |
| | | | | 85 | | | | | 90 | | | | | 95 | |
| Tyr | Ser | Gln | Pro | Gln | Phe | Arg | Ile | Lys | Gly | Gly | Leu | Phe | Ala | Asp | Ile |
| | | | 100 | | | | | 105 | | | | | 110 | | |
| Ala | Ser | His | Pro | Trp | Gln | Ala | Ala | Ile | Phe | Ala | Lys | His | Arg | Arg | Ser |
| | | | 115 | | | | 120 | | | | | 125 | | | |
| Pro | Gly | Glu | Arg | Phe | Leu | Cys | Gly | Gly | Ile | Leu | Ile | Ser | Ser | Cys | Trp |
| | 130 | | | | | 135 | | | | | 140 | | | | |
| Ile | Leu | Ser | Ala | Ala | His | Cys | Phe | Gln | Glu | Arg | Phe | Pro | Pro | His | His |
| 145 | | | | | 150 | | | | | 155 | | | | | 160 |
| Leu | Thr | Val | Ile | Leu | Gly | Arg | Thr | Tyr | Arg | Val | Val | Pro | Gly | Glu | Glu |
| | | | | 165 | | | | | 170 | | | | | 175 | |
| Glu | Gln | Lys | Phe | Glu | Val | Glu | Lys | Tyr | Ile | Val | His | Lys | Glu | Phe | Asp |
| | | | 180 | | | | | 185 | | | | | 190 | | |
| Asp | Asp | Thr | Tyr | Asp | Asn | Asp | Ile | Ala | Leu | Leu | Gln | Leu | Lys | Ser | Asp |
| | | | 195 | | | | 200 | | | | | 205 | | | |
| Ser | Ser | Arg | Cys | Ala | Gln | Glu | Ser | Ser | Val | Val | Arg | Thr | Val | Cys | Leu |
| | 210 | | | | | 215 | | | | | 220 | | | | |
| Pro | Pro | Ala | Asp | Leu | Gln | Leu | Pro | Asp | Trp | Thr | Glu | Cys | Glu | Leu | Ser |
| 225 | | | | | 230 | | | | | 235 | | | | | 240 |
| Gly | Tyr | Gly | Lys | His | Glu | Ala | Leu | Ser | Pro | Phe | Tyr | Ser | Glu | Arg | Leu |
| | | | | 245 | | | | | 250 | | | | | 255 | |
| Lys | Glu | Ala | His | Val | Arg | Leu | Tyr | Pro | Ser | Ser | Arg | Cys | Thr | Ser | Gln |
| | | | 260 | | | | | 265 | | | | | 270 | | |

| His | Leu | Leu | Asn | Arg | Thr | Val | Thr | Asp | Asn | Met | Leu | Cys | Ala | Gly | Asp |
|-----|-----|-----|-----|-----|-----|-----|-----|-----|-----|-----|-----|-----|-----|-----|-----|
|     |     | 275 |     |     |     | 280 |     |     |     | 285 |     |     |     |     |     |

| Thr | Arg | Ser | Gly | Gly | Pro | Gln | Ala | Asn | Leu | His | Asp | Ala | Cys | Gln | Gly |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Asp | Ser | Gly | Gly | Pro | Leu | Val | Cys | Leu | Asn | Asp | Gly | Arg | Met | Thr | Leu |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Val | Gly | Ile | Ile | Ser | Trp | Gly | Leu | Gly | Cys | Gly | Gln | Lys | Asp | Val | Pro |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |

| Gly | Val | Tyr | Thr | Lys | Val | Thr | Asn | Tyr | Leu | Asp | Trp | Ile | Arg | Asp | Asn |
|-----|-----|-----|-----|-----|-----|-----|-----|-----|-----|-----|-----|-----|-----|-----|-----|
|     |     |     | 340 |     |     |     | 345 |     |     |     |     |     | 350 |     |     |

| Met | Arg | Pro |
|-----|-----|-----|
|     |     | 355 |

( 2 ) INFORMATION FOR SEQ ID NO:7:

( i ) SEQUENCE CHARACTERISTICS:
        ( A ) LENGTH:1068 base pairs
        ( B ) TYPE:nucleic acid
        ( C ) STRANDEDNESS:double
        ( D ) TOPOLOGY:linear ( i i ) MOLECULE TYPE:DNA ( x i ) SEQUENCE DESCRIPTION: SEQ ID NO:7 :

| | | | | | | | | | | | | | |
|---|---|---|---|---|---|---|---|---|---|---|---|---|---|
| TCT | TAC | CAA | GAT | ACC | AGG | GCC | ACG | TGC | TAC | GAG | GAC | CAG | GGC | 42 |
| ATC | AGC | TAC | AGG | GGC | ACG | TGG | AGC | ACA | GCG | GAG | AGT | GGC | GCC | 84 |
| GAG | TGC | ACC | AAC | TGG | AAC | AGC | AGC | GCG | TTG | GCC | CAG | AAG | CCC | 126 |
| TAC | AGC | GGG | CGG | AGG | CCA | GAC | GCC | ATC | AGG | CTG | GGC | CTG | GGG | 168 |
| AAC | CAC | AAC | TAC | TGC | AGG | AAT | CCT | GAT | GGG | GAT | GCC | AAG | CCC | 210 |
| TGG | TGC | CAC | GTG | CTG | AAG | AAC | CGC | AGG | CTG | ACG | TGG | GAG | TAC | 252 |
| TGT | GAT | GTG | CCC | TCC | TGC | TCC | ACC | TGC | GGC | CTG | AGA | CAG | TAC | 294 |
| AGC | CAG | CCT | CAG | TTT | CGC | ATC | AAA | GGA | GGG | CTC | TTC | GCC | GAC | 336 |
| ATC | GCC | TCC | CAC | CCC | TGG | CAG | GCT | GCC | ATC | TTT | GCC | AAG | CAC | 378 |
| AGG | AGG | TCG | CCC | GGA | GAG | CGG | TTC | CTG | TGC | GGG | GGC | ATA | CTC | 420 |
| ATC | AGC | TCC | TGC | TGG | ATT | CTC | TCT | GCC | GCC | CAC | TGC | TTC | CAG | 462 |
| GAG | AGG | TTT | CCG | CCC | CAC | CAC | CTG | ACG | GTG | ATC | TTG | GGC | AGA | 504 |
| ACA | TAC | CGG | GTG | GTC | CCT | GGC | GAG | GAG | GAG | CAG | AAA | TTT | GAA | 546 |
| GTC | GAA | AAA | TAC | ATT | GTC | CAT | AAG | GAA | TTC | GAT | GAT | GAC | ACT | 588 |
| TAC | GAC | AAT | GAC | ATT | GCG | CTG | CTG | CAG | CTG | AAA | TCG | GAT | TCG | 630 |
| TCC | CGC | TGT | GCC | CAG | GAG | AGC | AGC | GTG | GTC | CGC | ACT | GTG | TGC | 672 |
| CTT | CCC | CCG | GCG | GAC | CTG | CAG | CTG | CCG | GAC | TGG | ACG | GAG | TGT | 714 |
| GAG | CTC | TCC | GGC | TAC | GGC | AAG | CAT | GAG | GCC | TTG | TCT | CCT | TTC | 756 |
| TAT | TCG | GAG | CGG | CTG | AAG | GAG | GCT | CAT | GTC | AGA | CTG | TAC | CCA | 798 |
| TCC | AGC | CGC | TGC | ACA | TCA | CAA | CAT | TTA | CTT | AAC | AGA | ACA | GTC | 840 |
| ACC | GAC | AAC | ATG | CTG | TGT | GCT | GGA | GAC | ACT | CGG | AGC | GGC | GGG | 882 |
| CCC | CAG | GCA | AAC | TTG | CAC | GAC | GCC | TGC | CAG | GGC | GAT | TCG | GGA | 924 |
| GGC | CCC | CTG | GTG | TGT | CTG | AAC | GAT | GGC | CGC | ATG | ACT | TTG | GTG | 966 |
| GGC | ATC | ATC | AGC | TGG | GGC | CTG | GGC | TGT | GGA | CAG | AAG | GAT | GTC | 1008 |
| CCG | GGT | GTG | TAC | ACA | AAG | GTT | ACC | AAC | TAC | CTA | GAC | TGG | ATT | 1050 |

CGT GAC AAC ATG CGA CCG                                               1068

( 2 ) INFORMATION FOR SEQ ID NO:8:

( i ) SEQUENCE CHARACTERISTICS:
        ( A ) LENGTH:356 amino acids
        ( B ) TYPE:amino acid
        ( D ) TOPOLOGY:linear ( i i ) MOLECULE TYPE:protein ( x i ) SEQUENCE DESCRIPTION: SEQ ID NO:8:

| Ser | Tyr | Gln | Asp | Thr | Arg | Ala | Thr | Cys | Tyr | Glu | Asp | Gln | Gly | Ile |
|---|---|---|---|---|---|---|---|---|---|---|---|---|---|---|
| 1 | | | | 5 | | | | | 10 | | | | | 15 |
| Ser | Tyr | Arg | Gly | Thr | Trp | Ser | Thr | Ala | Glu | Ser | Gly | Ala | Glu | Cys |
| | | | | 20 | | | | | 25 | | | | | 30 |
| Thr | Asn | Trp | Asn | Ser | Ser | Ala | Leu | Ala | Gln | Lys | Pro | Tyr | Ser | Gly |
| | | | | 35 | | | | | 40 | | | | | 45 |
| Arg | Arg | Pro | Asp | Ala | Ile | Arg | Leu | Gly | Leu | Gly | Asn | His | Asn | Tyr |
| | | | | 50 | | | | | 55 | | | | | 60 |
| Cys | Arg | Asn | Pro | Asp | Gly | Asp | Ala | Lys | Pro | Trp | Cys | His | Val | Leu |
| | | | | 65 | | | | | 70 | | | | | 75 |
| Lys | Asn | Arg | Arg | Leu | Thr | Trp | Glu | Tyr | Cys | Asp | Val | Pro | Ser | Cys |
| | | | | 80 | | | | | 85 | | | | | 90 |
| Ser | Thr | Cys | Gly | Leu | Arg | Gln | Tyr | Ser | Gln | Pro | Gln | Phe | Arg | Ile |
| | | | | 95 | | | | | 100 | | | | | 105 |
| Lys | Gly | Gly | Leu | Phe | Ala | Asp | Ile | Ala | Ser | His | Pro | Trp | Gln | Ala |
| | | | | 110 | | | | | 115 | | | | | 120 |
| Ala | Ile | Phe | Ala | Lys | His | Arg | Arg | Ser | Pro | Gly | Glu | Arg | Phe | Leu |
| | | | | 125 | | | | | 130 | | | | | 135 |
| Cys | Gly | Gly | Ile | Leu | Ile | Ser | Ser | Cys | Trp | Ile | Leu | Ser | Ala | Ala |
| | | | | 140 | | | | | 145 | | | | | 150 |
| His | Cys | Phe | Gln | Glu | Arg | Phe | Pro | Pro | His | His | Leu | Thr | Val | Ile |
| | | | | 155 | | | | | 160 | | | | | 165 |
| Leu | Gly | Arg | Thr | Tyr | Arg | Val | Val | Pro | Gly | Glu | Glu | Gln | Lys |
| | | | | 170 | | | | | 175 | | | | | 180 |
| Phe | Glu | Val | Glu | Lys | Tyr | Ile | Val | His | Lys | Glu | Phe | Asp | Asp | Asp |
| | | | | 185 | | | | | 190 | | | | | 195 |
| Thr | Tyr | Asp | Asn | Asp | Ile | Ala | Leu | Leu | Gln | Leu | Lys | Ser | Asp | Ser |
| | | | | 200 | | | | | 205 | | | | | 210 |
| Ser | Arg | Cys | Ala | Gln | Glu | Ser | Ser | Val | Val | Arg | Thr | Val | Cys | Leu |
| | | | | 215 | | | | | 220 | | | | | 225 |
| Pro | Pro | Ala | Asp | Leu | Gln | Leu | Pro | Asp | Trp | Thr | Glu | Cys | Glu | Leu |
| | | | | 230 | | | | | 235 | | | | | 240 |
| Ser | Gly | Tyr | Gly | Lys | His | Glu | Ala | Leu | Ser | Pro | Phe | Tyr | Ser | Glu |
| | | | | 245 | | | | | 250 | | | | | 255 |
| Arg | Leu | Lys | Glu | Ala | His | Val | Arg | Leu | Tyr | Pro | Ser | Ser | Arg | Cys |
| | | | | 260 | | | | | 265 | | | | | 270 |
| Thr | Ser | Gln | His | Leu | Leu | Asn | Arg | Thr | Val | Thr | Asp | Asn | Met | Leu |
| | | | | 275 | | | | | 280 | | | | | 285 |
| Cys | Ala | Gly | Asp | Thr | Arg | Ser | Gly | Gly | Pro | Gln | Ala | Asn | Leu | His |
| | | | | 290 | | | | | 295 | | | | | 300 |
| Asp | Ala | Cys | Gln | Gly | Asp | Ser | Gly | Gly | Pro | Leu | Val | Cys | Leu | Asn |
| | | | | 305 | | | | | 310 | | | | | 315 |
| Asp | Gly | Arg | Met | Thr | Leu | Val | Gly | Ile | Ile | Ser | Trp | Gly | Leu | Gly |
| | | | | 320 | | | | | 325 | | | | | 330 |

```
Cys Gly Gln Lys Asp Val Pro Gly Val Tyr Thr Lys Val Thr Asn
              335                 340                 345

Tyr Leu Asp Trp Ile Arg Asp Asn Met Arg Pro
              350                 355
```

( 2 ) INFORMATION FOR SEQ ID NO:9:

( i ) SEQUENCE CHARACTERISTICS:
       ( A ) LENGTH:105 nucleotides
       ( B ) TYPE:nucleic acid
       ( C ) STRANDEDNESS:double
       ( D ) TOPOLOGY:linear ( i i ) MOLECULE TYPE:DNA ( x i ) SEQUENCE DESCRIPTION: SEQ ID NO:9:

```
ATG GAT GCA ATG AAG AGA GGG CTC TGC TGT GTG CTG CTG CTG          42

TGT GGA GCA GTC TTC GTT TCG CCC AGC CAG GAA ATC CAT GCC          84

CGA TTC AGA AGA GGA GCC AGA                                     105
```

( 2 ) INFORMATION FOR SEQ ID NO:10:

( i ) SEQUENCE CHARACTERISTICS:
       ( A ) LENGTH:35 amino acids
       ( B ) TYPE:amio acid
       ( D ) TOPOLOGY:linear ( i i ) MOLECULE TYPE:peptide ( x i ) SEQUENCE DESCRIPTION: SEQ ID NO:10:

```
Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
                20                  25                  30

Gly Ala Arg
          35
```

( 2 ) INFORMATION FOR SEQ ID NO:11:

( i ) SEQUENCE CHARACTERISTICS:
       ( A ) LENGTH:5 amino acids
       ( B ) TYPE:amino acid
       ( C ) TOPOLOGY:linear ( i i ) MOLECULE TYPE:peptide ( i x ) FEATURE: Xaa is Lys or Arg ( x i ) SEQUENCE DESCRIPTION: SEQ ID NO:11:

```
Arg Ile Xaa Xaa Xaa
1               5
```

( 2 ) INFORMATION FOR SEQ ID NO:12:

( i ) SEQUENCE CHARACTERISTICS:
       ( A ) LENGTH:5 amino acids
       ( B ) TYPE:amino acid
       ( C ) TOPOLOGY:linear ( i i ) MOLECULE TYPE:peptide ( i x ) FEATURE: Xaa is Lys or Arg ( x i ) SEQUENCE DESCRIPTION: SEQ ID NO:12:

```
Ser Arg Xaa Xaa Xaa
1               5
```

( 2 ) INFORMATION FOR SEQ ID NO:13:

( i ) SEQUENCE CHARACTERISTICS:
        ( A ) LENGTH:5 amino acids
        ( B ) TYPE:amino acid
        ( C ) TOPOLOGY:linear ( i i ) MOLECULE TYPE:peptide ( i x ) FEATURE: Xaa is Lys or Arg ( x i ) SEQUENCE DESCRIPTION: SEQ ID NO:13:

Glu Arg Xaa Xaa Xaa
1                 5

( 2 ) INFORMATION FOR SEQ ID NO:14:

( i ) SEQUENCE CHARACTERISTICS:
        ( A ) LENGTH:5 amino acids
        ( B ) TYPE:amino acid
        ( D ) TOPOLOGY:linear ( i i ) MOLECULE TYPE:peptide ( i x ) FEATURE:Xaa is Lys or Arg ( x i ) SEQUENCE DESCRIPTION: SEQ ID NO:14:

Val Arg Xaa Xaa Xaa
1                 5

( 2 ) INFORMATION FOR SEQ ID NO:15:

( i ) SEQUENCE CHARACTERISTICS:
        ( A ) LENGTH:5 amino acids
        ( B ) TYPE:AMINO ACID
        ( D ) TOPOLOGY:linear ( i i ) MOLECULE TYPE:peptide ( x i ) SEQUENCE DESCRIPTION: SEQ ID NO:15:

Arg Ile Arg Lys Arg
1                 5

( 2 ) INFORMATION FOR SEQ ID NO:16:

( i ) SEQUENCE CHARACTERISTICS:
        ( A ) LENGTH:5 amino acids
        ( B ) TYPE:amino acid
        ( D ) TOPOLOGY:linear ( i i ) MOLECULE TYPE:peptide ( x i ) SEQUENCE DESCRIPTION: SEQ ID NO:16:

Ser Arg Lys Arg Arg
1                 5

( 2 ) INFORMATION FOR SEQ ID NO:17:

( i ) SEQUENCE CHARACTERISTICS:
        ( A ) LENGTH:5 amino acids
        ( B ) TYPE:amino acid
        ( D ) TOPOLOGY:linear ( i i ) MOLECULE TYPE:peptide ( x i ) SEQUENCE DESCRIPTION: SEQ ID NO:17:

Glu Arg Arg Lys Arg
1                 5

( 2 ) INFORMATION FOR SEQ ID NO:18:

( i ) SEQUENCE CHARACTERISTICS:
        ( A ) LENGTH:5 amino acids
        ( B ) TYPE:amino acid
        ( D ) TOPOLOGY:linear ( i i ) MOLECULE TYPE:peptide ( x i ) SEQUENCE DESCRIPTION: SEQ ID NO:18:

```
Val  Arg  Lys  Arg  Arg
 1                   5
```

( 2 ) INFORMATION FOR SEQ ID NO:19 :

( i ) SEQUENCE CHARACTERISTICS:
        ( A ) LENGTH:114 nucleotides
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:19:

```
GATCCGCCAC  CATGGATGCA  ATGAAGAGAG  GGCTCTGCTG  TGTGCTGCTG      50
CTGTGTGGAG  CAGTCTTCGT  TTCGCCCAGC  CAGGAAATCC  ATGCCCGATT     100
CAGAATCCGA  AAAA                                                114
```

( 2 ) INFORMATION FOR SEQ ID NO:20 :

( i ) SEQUENCE CHARACTERISTICS:
        ( A ) LENGTH:114 nucleotides
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:20:

```
GATCTTTTGC  GGATTCTGAA  TCGGGCATGG  ATTTCCTGGC  TGGGCGAAAC      50
GAAGACTGCT  CCACACAGCA  GCAGCACACA  GCAGAGCCCT  CTCTTCATTG     100
CATCCATGG  TGGCG                                                114
```

( 2 ) INFORMATION FOR SEQ ID NO:21 :

( i ) SEQUENCE CHARACTERISTICS:
        ( A ) LENGTH:114 nucleotides
        ( B ) TYPE:nucleic acid
        ( C ) STRANDEDNESS:double
        ( D ) TOPOLOGY:linear ( i i ) MOLECULE TYPE:DNA ( x i ) SEQUENCE DESCRIPTION: SEQ ID NO:21:

```
GATCCGCCAC  CATGGATGCA  ATGAAGAGAG  GGCTCTGCTG  TGTGCTGCTG      50
CTGTGTGGAG  CAGTCTTCGT  TTCGCCCAGC  CAGGAAATCC  ATGCCCGATT     100
CAGAATCCGA  AAAA                                                114
```

( 2 ) INFORMATION FOR SEQ ID NO:22:

( i ) SEQUENCE CHARACTERISTICS:
        ( A ) LENGTH: 287 nucleotides
        ( B ) TYPE:nucleic acid
        ( C ) STRANDEDNESS:double
        ( D ) TOPOLOGY:linear ( i i ) MOLECULE TYPE:DNA ( x i ) SEQUENCE DESCRIPTION: SEQ ID NO:22:

| AATTCACGCT | GTGGTGTTAT | GGTCGGTGGT | CGCTAGGGTG | 40 |
| CCGACGCGCA | TCTCGACTGC | ACGGTGCACC | AATGCTTCTG | 80 |
| GCGTCAGGCA | GCCAATCGGA | AGCTGTGGTA | TGGCTGTGCA | 120 |
| GGTCGTATAA | TCACCGCATA | ATTCGAGTCG | CTCAAGGCGC | 160 |
| ACTCCCGTTC | CGGATAATGT | TTTTGCTCC | GACATCATAA | 200 |
| CGGTTCCGGC | AAATATTCTG | AAATGAGCTG | TTGACAATTA | 240 |
| ATCATCGAAC | TAGTTAACTA | GTACGCAAGT | TCTCGTAAAA | 280 |
| AGGGTAT | | | | 287 |

( 2 ) INFORMATION FOR SEQ ID NO:23:

( i ) SEQUENCE CHARACTERISTICS:
        ( A ) LENGTH:36 nucleotides
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SE. ID NO:23:

GGAGCCAGAT CTTACCAAGG AAACAGTGAC TGCTAC      36

( 2 ) INFORMATION FOR SEQ ID NO:24 :

( i ) SEQUENCE CHARACTERISTICS:
        ( A ) LENGTH:40 nucleotides
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:24:

CAGTGACTGC TACTTTGGCC AGGGGTCAGC CTACCGTGGC      40

( 2 ) INFORMATION FOR SEQ ID NO:25:

( i ) SEQUENCE CHARACTERISTICS:
        ( A ) LENGTH: 46 nucleotides
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:25:

GGGTGCCTCC TGCCTCCCAT GGAATGGGTC CATGATCCTG ATAGGC      46

( 2 ) INFORMATION FOR SEQ ID NO:26:

( i ) SEQUENCE CHARACTERISTICS:
        ( A ) LENGTH: 46 nucleotides
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:26:

GGTTTACACA GCACAGAACG GCAGTGCACA GGCACTGGGCC TGGGC      46

( 2 ) INFORMATION FOR SEQ ID NO:27:

( i ) SEQUENCE CHARACTERISTICS:
        ( A ) LENGTH: 38 nucleotides
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:27:

GAGCCAGATC TTACCAAGAT ACCAGGGCCA CGTGCTAC      3 8

( 2 ) INFORMATION FOR SEQ ID NO:28:

( i ) SEQUENCE CHARACTERISTICS:
        ( A ) LENGTH: 46 nucleotides
        ( B ) TYPE:nucleic acid
        ( C ) STRANDEDNESS:single
        ( D ) TOPOLOGY:linear ( i i ) MOLECULE TYPE:DNA ( i i i ) SEQUENCE DESCRIPTION:SEQ ID NO:28:

GGGGAACCAC AACTACTGCA GGAATCCTGA TGGGGATGCC AAGCCC      4 6

COMPOUNDS AND METHODS FOR TREATMENT OF THROMBOEMBOLIC DISORDERS

This application is a division of application Ser. No. 07/689,410, filed Apr. 22, 1991, now abandoned.

FIELD OF INVENTION

This invention is in the field of molecular biology. The invention provides diglycosylated tissue plasminogen activator derivatives, DNA compounds that encode these diglycosylated tissue plasminogen activator derivatives, recombinant DNA vectors, host cells transformed with these vectors, and methods for the production of the diglycosylated tissue plasminogen activator derivatives. The invention further provides methods and compositions useful in the treatment of thromboembolic disorders.

BACKGROUND OF THE INVENTION

Plasminogen activators are a unique class of enzymes that convert plasminogen to its active enzymatic form, plasmin. Plasmin is a serine protease that degrades the fibrin network of blood clots. Several plasminogen activators are currently being used as in vivo fibrinolytic agents in the treatment of acute myocardial infarction (Tienfenbrunn et al., 1989, *Fibrinolysis* 3:1–15). One of these plasminogen activators, tissue plasminogen activator (t-PA), has a significantly enhanced ability to activate plasminogen in the presence of fibrin (Hoylaerts et al., 1982, *J. Biol. Chem.* 257:2912–2919. Thus, when used as an in vivo fibrinolytic agent, t-PA is directed to fibrin clots.

Human t-PA is a multi-domain serine protease secreted by vascular endothelial cells. The DNA and amino acid structure of human t-PA was described by Pennica et al., 1983, *Nature* 301:214. Based on the cDNA sequence of t-PA, the inferred sequence of 527 amino acids comprises five distinct structural domains. Gene mapping studies of genomic t-PA have shown that the gene encoding t-PA is comprised of twelve exons split by introns (Ny et al., 1984, *Proc. Natl. Acad. Sci. USA* 81:5355). These introns correspond, in part, with the domain junctions at the amino acid level.

When synthesized by the cell, t-PA comprises a 35 amino acid signal peptide/propeptide region. The signal peptide directs secretion of the t-PA molecule from the cell. The signal peptide/propeptide region in cleaved from the t-PA molecule to yield the 527 amino acid t-PA molecule.

The amino-terminal portion of the t-PA molecule contains a disulfide-linked loop referred to as the Finger domain (F). The second domain, called the Growth Factor domain (E or GF), is highly homologous with epidermal growth factor. The third and fourth domains are highly disulfide-linked structures referred to as Kringles (K1 and K2). The fifth domain, located at the carboxy-terminus, is the Serine Protease domain (SP).

There has been significant growth in the acceptance of thrombolytic therapy for the early restoration of blood flow to ischemic myocardium. However, because of a short plasma half-life, tissue plasminogen activator must be administered by intravenous infusion to insure thrombolytic efficacy. Recent reviews of coronary thrombolysis suggest that the ideal properties of a new thrombolytic agent are that it be fibrin specific, have a longer plasma half-life allowing for a single injection administration, produce more rapid reperfusion, prevent reocclusion and be safer (i.e. lower bleeding risk, non-immunogenic), than streptokinase, t-PA or urokinase (Collen, D., 1988, *Klin. Wochenschr.* 66 (Suppl. 12) 15–23; Bang et al., 1989, *Annu. Rev. Pharmacol. Toxicol.* 29:322–341; Minno et al., 1989, *Pharmacol. Res.* 21(2):153–161; Mueller et al., 1989, *Med. Clin. North Am.* 73(2):387–407).

Since the introduction of recombinant human t-PA, investigators have produced modified recombinant derivatives of t-PA (Van Zonneveld, et al., 1986, *Proc. Natl. Acad. Sci. U.S.A.* 83:4670–4674; Krause, J., 1988, *Fibrinolysis* 2:133–142; Pannekoek et al., 1988, *Fibrinolysis* 2:123–133. Haigwood et al., 1989, *Protein Engineering* 2:611–620; Higgins and Bennett, 1990, *Annu. Rev. Pharmacol. Toxicol.* 30:91). A major emphasis in the design of derivative forms has been to increase fibrin specificity, increase circulating plasma half-life, and decrease bleeding liability compared with the t-PA molecule.

One derivative of t-PA was described by Burck et al., 1990, *Journal of Biological Chemistry* 265(9):5176. This derivative, known as mt-PA6, was constructed by site-specific mutagenesis of the cDNA encoding human t-PA. The DNA encoding amino acids 4–175 was deleted so that upon expression the resultant t-PA derivative sequentially comprised the signal peptide and propeptide regions of t-PA, the first three amino acids of t-PA, the Kringle 2 domain and the Serine Protease domain. Upon secretion from a eucaryotic host cell, the signal peptide and propeptide regions are cleaved from the molecule. mt-PA6 was found to posses greater fibrinolytic activity and a greater ability to activate thrombus-bound plasminogen than t-PA (Jackson et al., 1990, *Circulation* 82:930–940). The DNA sequence of mt-PA6 is presented as SEQ. ID. NO: 1. The amino acid sequence of mt-PA6 is presented as SEQ. ID. NO: 2. The DNA encoding the signal peptide and propeptide regions is homologous to that of t-PA and is positioned directly adjacent to (in the 5' direction) the DNA encoding the t-PA molecule. This DNA sequence is presented as SEQ. ID. NO: 9. The amino acid sequence of the signal peptide and propeptide regions is presented as SEQ. ID. NO: 10.

Human t-PA comprises four consensus Asparagine-linked (N-linked) glycosylation sites at amino acids 117, 184, 218 and 448. N-linked glycosylation sites are tripeptide sequences that are specifically recognized and glycosylated. Examples of tripeptide consensus sequences include asparagine-X-serine and asparagine-X-threonine. In t-PA, amino acid 184 in the Kringle 2 domain is glycosylated only part of the time while amino acid 218 is not glycosylated (Higgins and Bennett, supra.). Thus, two glycosylation forms of t-PA have been isolated. One form is glycosylated at amino acid 117 in the Kringle 1 domain and amino acid 448 in the Serine Protease domain. The second form is glycosylated at amino acids 117, 184 and 448. The ologosaccharides at amino acids 184 and 448 are complex ologosaccharides, while amino acid 117 is occupied by a high-mannose oligosaccharide (Spellman et al., 1989, *J. of Biol. Chem.* 264(24):14100).

When produced by eucaryotic cell culture, mt-PA6 is also found in two glycosylation forms. These two forms account for the doublet of 40 and 42 kD bands seen when the purified enzyme is analyzed by gel electrophoresis. Primary mt-PA6 (mt-PA6-P) is glycosylated at amino acid 276 (equivalent to amino acid 448 of t-PA) but not at amino acid 12 (equivalent to amino acid 184 of t-PA). Variant mt-PA6 (mt-PA6-V) is glycosylated at amino acids 276 and 12. mt-PA6 lacks the K1 domain and, therefore, lacks the glycosylation site present in this domain. As with t-PA, no glycosylation occurs at amino acid 46 (equivalent to amino acid 218 of t-PA) in the Kringle 2 domain. mt-PA6-V comprises 15–25% of the mt-PA6 molecules secreted from the Syrian hamster cell line AV12-664 (Burck et al., supra).

The thrombolytic potential of mt-PA6-V was studied in a canine thrombosis model. The canine thrombosis model was described by Jackson et al., supra. The role of mt-PA6-V in fibrinogen degradation and plasminogen degradation was also examined by methods described by Jackson et al., supra. These studies demonstrated that diglycosylated t-PA derivatives lacking the Finger, GF and Kringle 1 domains, such as mt-PA6-V, provide advantages over their partially and nonglycosylated counterparts in the treatment of thromboembolic disorders. mt-PA6-V displays the unexpected and advantageous property of causing less systemic conversion of plasminogen to plasmin. mt-PA6-V is markedly less prone to metabolism to its two-chain form, and has a higher fibrinolytic versus fibrinogenolytic ratio than mt-PA6-P. Surprisingly, mt-PA6-V also provides a greater maintenance of coronary blood flow. Methods for the use of diglycosylated forms of t-PA derivatives that lack the Finger, Growth Factor and Kringle 1 domains in the treatment of thromboembolic disorders are disclosed by U.S. patent application Ser. No. 07/633,584, Attorney Docket X-7870, filed Dec. 24, 1990.

As noted above, glycosylation at amino acid 184 of t-PA, or the equivalent position in other t-PA derivatives such as mt-PA6, occurs in only a small portion of the molecules. For example, mt-PA6-V comprises only 15%–25% of the mt-PA6 molecules secreted from a Syrian Hamster cell line (Burck et al., supra.). In view of the beneficial properties of diglycosylated forms of t-PA derivatives that lack the Finger, Growth Factor and Kringle 1 domains, it would be advantageous to be able to produce a homogeneous population of these diglycosylated t-PA derivative from a host cell.

The present invention addresses this need by providing novel diglycosylated t-PA derivatives. The invention further provides DNA compounds, expression vectors and transformed host cell which enable the production of a homogeneous population of these derivatives. The invention further provides methods and compositions for the treatment of thromboembolic disorders.

For purposes of the present invention, as disclosed and claimed herein, the following terms are defined below.

ApR—the ampicillin-resistant phenotype or gene conferring same.

E1A—an immediate-early gene product of adenovirus which can activate a poly-GT element to express enhancer activity and can activate the BK virus enhancer.

ep—a DNA segment comprising the SV40 early promoter of the T-antigen gene, the T-antigen binding sites, and the SV40 origin of replication.

GBMT transcription control unit—a modified transcription control unit that comprises the P2 enhancer element of BK virus spaced closely to the upstream regulatory element of the major late promoter of adenovirus (MLTF), the adenovirus-2 major late promoter and a poly-GT element positioned to stimulate said promoter and a DNA sequence encoding the spliced tripartite leader of adenovirus-2. The GMBT transcription control unit is best exemplified by the approximately 900 base pair HindIII cassette found in plasmid pGTC which is found in *Escherichia coli* K-12 AG1/pGTC (NRRL B-18593).

GT—enhancer system—any poly-GT element linked to a promoter, such as MLP, in which the poly-GT element does not itself possess enhancer activity but is activated as an enhancer by an immediate-early gene product of a large DNA virus, such as the E1A gene product or by any similarly activating viral gene product.

HmR—the hygromycin-resistant phenotype or gene conferring same.

IVS—DNA encoding an introns, also called an intervening sequence.

Large DNA virus—a virus that infects eucaryotic cells and has a genome greater than ~10 kb in size, i.e., any of the pox viruses, adenoviruses, and herpes viruses.

MLP—the major late promoter of adenovirus, that is also referred to herein as the adenovirus late promoter, adenovirus-type-2 late promoter, or Ad2 late promoter.

MLTF binding site—the site in adenovirus DNA where the major late transcription factor (MLTF) binds; the MLTF is required for MLP activity.

Glycosylation—the attachment of oligosaccharides to a protein through an N-glycosidic bond with the asparagine residue in an Asn-X-Ser/Thr sequence.

NeoR—the neomycin resistance-conferring gene, which can also be used to confer G418 resistance in eucaryotic host cells.

ori—a plasmid origin of replication.

pA—a DNA sequence encoding a polyadenylation signal.

Poly-GT element—a DNA sequence of (GT)n-(CA)n, which is illustrated herein by a sequence where n is 21, but which can also refer to sequences of varying lengths where n is greater or less than 21, and may refer to chemically synthesized (GT)n-(CA)n sequences or human genomic DNA fragments containing a (GT)n-(CA)n tract.

Reocclusion—complete cessation of blood flow after successful thrombolysis caused by reformation of thrombus and/or vasoconstriction.

Reperfusion—restoration of blood flow caused by successful thrombolysis.

SUMMARY

Figure 1:
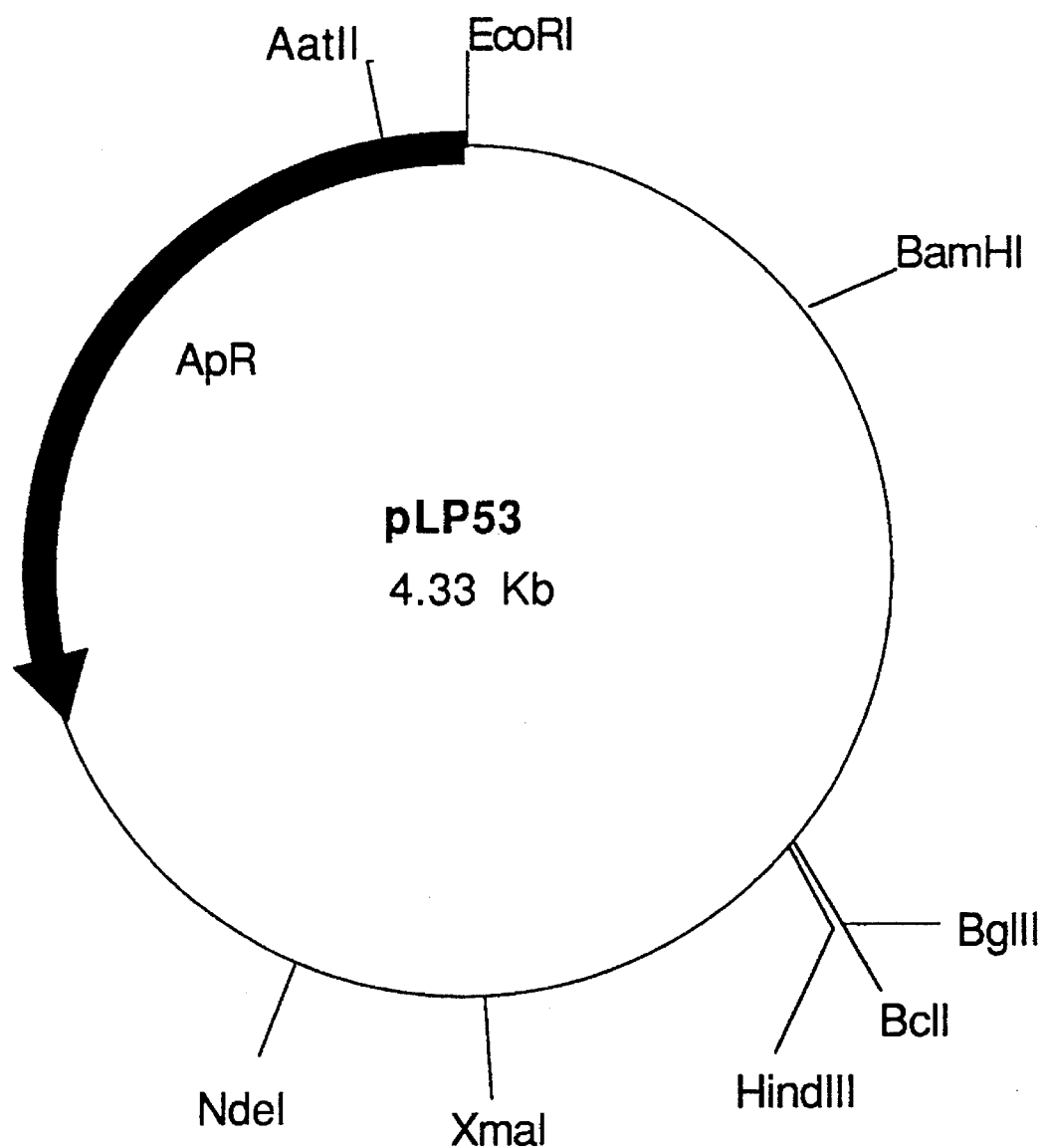
FIG. 1 is a restriction and function map of pLP53.

The present invention provides novel tissue plasminogen activator derivatives that lack the Finger, Growth Factor and Kringle 1 domains and comprise a Kringle 2 domain that is monoglycosylated at a site other than that of t-PA. In addition, the invention provides t-PA derivatives that lack the Finger, Growth Factor, Kringle 1 and Kringle 2 domains and comprise a chimeric Kringle domain that is capable of being glycosylated. The invention also provides DNA compounds that encode the above t-PA derivatives, recombinant DNA vectors, host cells transformed with these vectors, and methods for the production of the diglycosylated t-PA derivatives. The invention further provides methods and compositions for the treatment of thromboembolic disorders.

DETAILED DESCRIPTION

The present invention provides derivatives of tissue plasminogen activator that lack the Finger, Growth Factor and Kringle 1 domains and comprise a Kringle 2 domain that is monoglycosylated at a site other than that of t-PA. Using recombinant DNA techniques, an alternate glycosylation sequence is provided within the Kringle 2 domain of these t-PA derivatives. This alternate glycosylation consensus sequence, as well as the glycosylation consensus sequence within the Serine Protease domain, is glycosylated upon the expression and secretion of these molecules from eucaryotic host cells. Thus, a homogeneous population of diglycosylated t-PA derivatives that lack the Finger, Growth Factor and Kringle 1 domains is produced.

In a preferred embodiment of the invention, the DNA sequence encoding the glycosylation consensus sequence at the amino acid equivalent to position 184 in the Kringle 2 domain of t-PA was altered such that glycosylation at this amino acid was prevented. The DNA sequence encoding the Kringle 2 domain was then further altered to provide a glycosylation consensus sequence at an alternate site within the Kringle 2 domain. For example, the consensus sequence for glycosylation was provided at the amino acids surrounding the amino acid equivalent to either position 205 or 219 of t-PA. The alternate glycosylation site within the Kringle 2 domain enables the production of a homogeneous population of the diglycosylated t-PA derivative molecules by a eucaryotic host cell.

In a more preferred embodiment of the invention, a derivative of mt-PA6 that is monoglycosylated at a site within the Kringle 2 domain other than that of t-PA is provided. Examples of such derivatives of mt-PA6 include the molecules mt-PA6-D and mt-PA6-E.

mt-PA6-D comprises an alternate glycosylation consensus sequence at the amino acids surrounding position 33 (equivalent to amino acid 205 of t-PA). The DNA sequence encoding mt-PA6-D is provided as SEQ. ID. NO: 3. The amino acid sequence of mt-PA6-D is provided as SEQ. ID. NO: 4. mt-PA6-D is the most preferred embodiment of the present invention.

mt-PA6-E comprises an alternate glycosylation consensus sequence at the amino acids surrounding position 48 (equivalent to amino acid 219 of t-PA). The DNA sequence encoding mt-PA6-E is provided as SEQ. ID. NO: 5. The amino acid sequence of mt-PA6-E is provided as SEQ. ID. NO: 6.

In another embodiment of the present invention, a novel DNA compound encoding a derivative t-PA molecule, called mt-PA9, was constructed. The DNA molecule encodes the signal peptide and propeptide regions of t-PA, the first three amino acids of t-PA, a chimeric Kringle domain comprised of the first exon of the Kringle 1 domain and the second exon of the Kringle 2 domain, and the Serine Protease domain of t-PA. DNA encoding mt-PA9 no longer encodes the variable glycosylation site at the amino acid equivalent to position 184 of Kringle 2, but now contains the obligatory glycosylation site located in the first exon of Kringle 1. Thus, the present invention provides for the production of a human t-PA derivative that lacks the Finger, Growth Factor, Kringle 1, and Kringle 2 domains and comprises a chimeric Kringle domain, said chimeric Kringle domain comprising: a portion of the Kringle 1 domain that is capable of being glycosylated; and a portion of the Kringle 2 domain that is not capable of being glycosylated. The DNA sequence encoding mt-PA9 is presented as SEQ. ID. NO: 7. The amino acid sequence of mt-PA9 is presented as SEQ. ID. NO: 8.

The method of producing the novel t-PA derivatives of the present invention comprises culturing a host cell transformed with a DNA compound that encodes a t-PA derivative of the invention under conditions that allow the expression of the t-PA derivative. The t-PA derivative is secreted from the host cell and isolated from the culture medium.

The skilled artisan will recognize that the DNA compounds which encode the novel t-PA derivatives of the present invention comprise DNA encoding signal peptide and propeptide regions which provide for the secretion of the t-PA molecule from the host cell. The DNA encoding the signal peptide and propeptide regions may be homologous to that of t-PA, and will be positioned directly adjacent to (in the 5' direction) the DNA encoding the t-PA derivative. The DNA sequence of the signal peptide and propeptide regions of t-PA is presented as SEQ. ID. NO: 9. The amino acid sequence of the signal peptide and propeptide regions of t-PA is presented as SEQ. ID. NO: 10.

Amino acids −13 to −35 of the t-PA signal peptide are hydrophobic amino acids that directs secretion of the t-PA molecule from the host cell (Vehar et al., 1984, *Bio/Technology* 2(12):1050). This signal sequence is cleaved from the t-PA molecule during the secretion process, yielding a t-PA molecule with a 12 amino acid propeptide extension at the amino-terminal end. When t-PA is produced by melanoma cells using cell culture techniques, the t-PA molecules isolated from the resulting culture medium exit in two forms (Wallen et al., 1983, *Eur. J. Biochem.* 132:681–686). One form is a t-PA molecule from which 9 of the 12 amino acids of the propeptide have been cleaved, resulting in a t-PA molecule with the tripeptide amino-terminal extension $H_2N$-Gly-Ala-Arg. A second form is a fully processed t-PA from which the entire propeptide region has been cleaved (Vehar et al., supra.). mt-PA6 is also found in culture medium in the partially and fully processed forms. No differences were observed in the in vitro activity of the two amino-terminus forms of mt-PA6 (Burck et al., supra).

The heterogeneity at the amino-terminus may be eliminated by providing a propeptide region that is capable of being uniformly cleaved by a cell associated protease. U.S. patent application Ser. No. 07/609,510, Attorney Docket X-7809, filed Nov. 6, 1990, describes compounds and methods that allow production of a homogeneous population of t-PA molecules. These sequences are positioned to directly precede amino acid +1 (Ser) of the t-PA molecule and to replace the corresponding amino acids in the t-PA propeptide region. The amino acid sequence of the propeptide cleavage site can be encoded by the following amino acid sequences: Arg Ile Xaa Xaa Xaa (SEQ. ID. NO: 11); Ser Arg Xaa Xaa Xaa (SEQ. ID. NO: 12); Glu Arg Xaa Xaa Xaa (SEQ. ID. NO: 13); and Val Arg Xaa Xaa Xaa (SEQ. ID. NO: 14), wherein amino acids at positions labelled Xaa are Lys or Arg. The more preferred uniformly cleavable cell associated protease cleavage sites are: Arg Ile Arg Lys Arg (SEQ. ID. NO: 15); Ser Arg Lys Arg Arg (SEQ. ID. NO: 16); Glu Arg Arg Lys Arg (SEQ. ID. NO: 17); Val Arg Lys Arg Arg (SEQ. ID. NO: 18). The most preferred uniformly cleavable cell associated protease cleavage sequence is SEQ. ID. NO: 15. The DNA sequence encoding these cleavage sequences can be incorporated into the recombinant DNA vectors encoding the t-PA molecules. The skilled artisan will recognize that incorporation of these DNA sequences can be carried out by methods well known in the art, such as site-specific mutagenesis (described by Maniatis et al., *Molecular Cloning: A Laboratory Manual* Cold Spring Harbor N.Y. (2d ed. 1989) and Zoller and Smith, 1984, *DNA* 3:479–488). Thus, the compounds of the present invention can be produced such that the amino-terminus of the molecules lacks the tripeptide sequence H₂N-Gly-Ala-Arg.

To further exemplify the present invention, the plasmids pGT-t6D-d and pGT-t6E-d were constructed. Each of these plasmids enables high level expression of a diglycosylated form of a t-PA derivative that lacks the Finger, Growth Factor and Kringle 1 domains, linked to a uniformly cleavable propeptide region (SEQ. ID. NO: 15). Expression is provided by these plasmids from the GBMT unit that comprises the P2 enhancer of BK virus spaced closely to the upstream regulatory element of the major late promoter of adenovirus (MLTF), the adenovirus-2 late promoter, a poly-GT element positioned to stimulate said promoter and a DNA sequence encoding the spliced tripartite leader sequence of adenovirus. When properly positioned, the GBMT unit drives high level expression of the diglycosylated t-PA derivatives. The plasmid pGT-t6D-d has the GMBT unit properly positioned to express the t-PA derivative mt-PA-6-D. The plasmid pGT-t-6E-d has the GBMT unit properly positioned to express the t-PA derivative mt-PA-6-E.

The above expression vectors were constructed as follows. The DNA encoding mt-PA6 from plasmid pL229 (construction described in Example 2) was cloned into the BamHI restriction enzyme site of plasmid pTZ18U (available from Bio-Rad Laboratories, Hercules Calif. 94547) to form the plasmid pTZ-t-6. Plasmid pTZ-t6 was subjected to several rounds of site specific mutagenesis.

In the first round of site specific mutagenesis, the DNA encoding amino acid 12 of mt-PA6 in plasmid pTZ-t6 was converted from an asparagine to a glutamine. This mutation destroyed the glycosylation consensus sequence located at this site. This mutated plasmid was then subjected to subsequent rounds of mutagenesis to create a glycosylation consensus sequence at an alternate site within the Kringle 2 domain of the mutated mt-PA6 encoding DNA.

One of the plasmids formed from a subsequent round of site-specific mutagenesis of plasmid pTZ-t6 was the plasmid pTZ-t6D. In addition to the asparagine to glutamine conversion at amino acid 12, this plasmid was mutated to provide DNA encoding a glycine residue inserted between amino acids 33 and 34 of mt-PA6. This mutation provides a consensus glycosylation sequence at this site within the Kringle 2 domain. Plasmid pTZ-t6D encodes a derivative of mt-PA6, called mt-PA6-D.

Another of the plasmids formed from a subsequent round of site-specific mutagenesis of plasmid pTZ-t6 was the plasmid pTZ-t6E. In addition to the asparagine to glutamine conversion at amino acid 12, this plasmid was mutated to convert the DNA encoding the proline residue at position 48 to a codon encoding glycine. This mutation provides a consensus glycosylation sequence at this site within the Kringle 2 domain. Plasmid pTZ-t6E encodes a derivative of mt-PA6, called mt-PA6-E.

The DNA encoding the derivatives mt-PA6-D or mt-PA6-E in plasmid pTZ-t6D or pTZ-t6E, respectively, was cloned into the 3273 base pair XmaI-BglII restriction fragment of plasmid pLP53-TLB to form plasmid pTLB-t6D and plasmid pTLB-t6E. Plasmids pTLB-t6D and pTLB-t6E contain DNA encoding mt-PA6-D or mt-PA6-E linked to the novel propeptide region SEQ. ID. NO: 15.

Subsequently, the 1007 base pair XmaI-BglII restriction fragment encoding mt-PA6-D from the plasmid pTLB-t6D was ligated with the 3865 base pair AatII-XmaI restriction fragment of plasmid pmt6-hd and the 3560 base pair BclII-AatII restriction fragment of plasmid pGTC to form the expression plasmid pGT-t6D-d. Plasmid pGT-Bt6D-E was constructed by the same method as described for pGT-t6D-d except that 1007 base pair XmaI-BglII restriction fragment encoding mt-PA6-E from plasmid pTLB-t6E was substituted for the DNA encoding mt-PA6-D. The construction of plasmid pmt6-hd is described in Example 2. The plasmid GTC can be conventionally isolated from *Escherichia coli* K12 AG1/pGTC, a culture deposited on Jan. 18, 1990 and made part of the permanent stock culture collection of the Northern Regional Research Center (NRRL), Agricultural Research Service, United States Department of Agriculture, Peoria, Ill. 61604, under accession number NRRL B-18593. A restriction site and function map of plasmid pGTC is presented in FIG. 9.

The t-PA derivative mt-PA9 was constructed as follows. The 1881 base pair BamHI restriction fragment of plasmid pTPA603 (construction described in Example 2) was cloned into the BamHI restriction site of the replicative form (RF) of the bacteriophage vector M13mp18 to form the vector, M13t-PA. Plasmid M13nt-PA, which contains the DNA encoding t-PA, was subjected to site-specific mutagenesis to delete exons 4, 5, 7, and 8 of the t-PA molecule. The resulting vector, M13t-PA9, contains DNA encoding a t-PA derivative that comprises a Serine Protease domain and a chimeric Kringle domain comprised of the first exon of the Kringle 1 domain and the second exon of the Kringle 2 domain. Thus, the DNA encoding mt-PA9 comprises DNA encoding the signal peptide and propeptide regions, the first three amino acids of t-PA, amino acids 87–145 of the Kringle 1 domain, and amino acids 233–527 of t-PA.

The above t-PA derivatives are illustrative of the compounds of the present invention. The skilled artisan will recognize that diglycosylated t-PA derivatives other than those specifically listed above are also within the scope of the present invention. By way of example, such t-PA derivatives include the following derivatives, in which the variable glycosylation site at the amino acid equivalent to position 184 of t-PA is eliminated and an alternate glycosylation site is introduced into the Kringle 2 domain. For example, the amino acid glycine at the position equivalent to amino acid 185 of t-PA may be eliminated in order to disrupt the consensus glycosylation sequence and, thus, prevent glycosylation at the position equivalent to amino acid 184 of t-PA. In conjunction with the elimination of the variable glycosylation site at this position, the following changes may be introduced to provide an alternate glycosylation site. The amino acid glycine or serine may be inserted between the amino acids equivalent to positions 205 and 206 of t-PA. As another alternative, the amino acid proline at the position equivalent to position 219 of t-PA may be converted to the amino acid glycine. Elimination and insertion of DNA sequences can be carried out by various techniques known to the skilled artisan, such as site-specific mutagenesis.

Many modifications of the present illustrative DNA sequences and plasmids are possible. For example, the degeneracy of the genetic code allows for the substitution of nucleotides throughout the polypeptide coding regions, as well as in the translational stop signal, without alteration of the encoded polypeptide coding sequence. Such substitutable sequences can be deduced from the known amino acid or DNA sequence of human t-PA and can be constructed by conventional synthetic or site-specific mutagenesis procedures. Synthetic DNA methods can be carried out in substantial accordance with the procedures of Itakura et al., 1977, *Science* 198:1056 and Crea et al., 1978, *Proc. Natl Acad. Sci. USA* 75:5765. The skilled artisan will recognize that the vectors described herein merely exemplify the wide variety of vectors which can be constructed to contain the novel t-PA derivatives of this invention. Numerous vectors may be constructed to contain the appropriate regulatory elements necessary to express the DNA encoding the novel t-PA derivatives in the eucaryotic host cells. Examples of such vectors are described by Maniatis et al., supra., and in *Eucaryotic Viral Vectors*, edited by Gluzman, published by Cold Spring Harbor Laboratories, Cold Spring Harbor New York, 1982.

It is preferable to transform the vectors exemplified herein into host cells that express the adenovirus E1A immediate-early gene product, in that the BK enhancer found on the vectors functions to enhance expression most efficiently in the presence of E1A. Skilled artisans will recognize that a number of host cells express, or can be made to express, an immediate-early gene product of a large DNA virus such as E1A. Preferred cell lines are the Syrian Hamster line AV12-664 (available from the American Type Culture Collection (ATCC), Rockville Md., 20852 under the accession number CRL 9595) or the human kidney 293 cell line (ATCC CRL 1573). The AV12-664 cell line is most preferred. However, the vectors of the present invention can be transformed into and expressed in a variety of eucaryotic host cells. Exemplary host cells suitable for use in the invention include BHK-21 cells (ATCC CRL 10), CHO-K1 cells (ATCC CRL 61) and C1271 cells (ATCC CRL 1616). Those skilled in the art will recognize that many eucaryotic host cells possess the necessary cellular machinery for the recognition and processing of the signal peptide and propeptide regions on the nascent proteins of the invention and provide the post-translational modifications, such as glycosylation.

After transformation of a vector of the present invention into a eucaryotic host cell, one can select transformants on the basis of a selectable phenotype. This phenotype can be conferred either by a selectable marker present on the expression vector or present on another vector cotransformed with the expression vector into the host cell. Once transformants are selected, it is desirable to identify which transformants are expressing the highest levels of the desired protein encoded on the expression vector. Such identification is especially important after a cotransformation procedure, which generates a number of transformants that contain only the plasmid containing the selectable marker and so do not contain the expression vector.

Vectors of the invention that possess no selectable marker with which to identify and isolate stable eucaryotic transformants are useful not only for purposes of transient assay but also for purposes of cotransformation, a procedure disclosed in U.S. Pat. No. 4,399,216, issued Aug. 26, 1983, and incorporated herein by reference. In addition, the vectors may further comprise sequences that allow for replication in *Escherichia coli*, as it is usually more efficient to prepare plasmid DNA in *E. coli* than in other host organisms.

The diglycosylated form of the t-PA derivatives of the present invention can be isolated by affinity chromatography in substantial accordance with the method by Einarsson et al., 1985, *Biochim. Biophys. Acta* 830:1–10, and Rijken et al., 1985, *Thromb. and Haemostas.* 54(4), 788–791 or as described in Example 12.

The diglycosylated t-PA derivatives of the present invention will be useful in the treatment of a variety of thromboembolic disorders. Such disorders include deep vein thrombosis, disseminated intravascular coagulation, emboli orginating from the heart or peripheral arteries, acute myocardial infarction, thrombotic strokes, and fibrin deposits associated with invasive cancers. Thromboembolic disorders can be treated by administration of a thrombolytically effective dose of the diglycosylated derivatives of the present invention.

The diglycosylated t-PA derivatives of the present invention can be formulated according to known methods to prepare pharmaceutically useful compositions, whereby the diglycosylated t-PA derivative is combined in admixture with pharmaceutically acceptable carrier vehicle. Suitable carrier vehicles and their formulation, inclusive of other human proteins, e.g., human serum albumin, are described, for example, in *Remington's Pharmaceutical Sciences* 16th ed., 1980, Mack Publishing Co., edited by Oslo et al. Such compositions will contain an effective amount of a diglycosylated t-PA derivative of the present invention together with a suitable amount of carrier vehicle to prepare pharmaceutical compositions suitable for effective administration to the patient. Such compositions can be administered parentally, or by other means that ensure its delivery to the bloodstream in an effective form. The preferred method of administration of the diglycosylated t-PA derivatives of the present invention is by bolus intravenous administration. Preferred dosages range from about 0.01 mg/kg to 10 mg/kg. More preferred dosages range from about 0.1 mg/kg to 1 mg/kg. The most preferred dosage is about 0.4 mg/kg.

The following examples are intended to assist in further understanding of the invention. Particular materials employed, species and conditions are intended to be further illustrative of the invention and not limiting the reasonable scope thereof. Enzymes referred to in the examples are available, unless otherwise indicated from Bethesda Research Laboratories (BRL), Gaithersburg, Md. 20877, New England Biolabs Inc. (NEB), Beverly, Mass. 01915, or Boehringer Mannheim Biochemicals (BMB), 7941 Castleway Drive, Indianapolis, Ind. 46250 and are used in substantial accordance with the manufacturer's recommendations. Many of the techniques employed herein are well known to the artisan of ordinary skill. Molecular biology techniques are described in detail in laboratory manuals such as Maniatis et al., supra, and *Current Protocols in Molecular Biology* (Ausubel et al. eds. 1987). The skilled artisan will recognize that alternate procedures can be substituted for various procedures presented below.

EXAMPLE 1

Construction of pLP53-TLB

A. Preparation of BamHI-BglII Digested pLP53

The plasmid pLP53 can be conventionally isolated from *Escherichia coli* K12 AG1/pLP53 according to the method of Example 1E. *E. coli* K12 AG1/pLP53 was deposited on Sep. 21, 1990 and made part of the permanent stock culture collection of the Northern Regional Research Center (NRRL), Agriculture Research Service, U.S. Department of Agriculture, Peoria, Ill. 61604 under accession number NRRL B-18714. A restriction site and function map of pLP53 is shown in FIG. 1.

Five µl (5 µg) of pLP53 DNA was digested to completion with 2 µl (20 units) of BamHI and 2 µl (20 units) BglII in a 50 µl reaction volume containing 50 mM Tris-HCl (pH 8.0)

(Tris is tris [hydroxymethyl]aminomethane), 10 mM $MgCl_2$ and 50 mM NaCl. The sample was incubated at 37° C. for two hours. The sample was extracted twice with an equal volume of a mixture of phenol and chloroform (50:50) and the aqueous layer was recovered. The DNA was recovered from the aqueous layer by the addition of 0.1 volume of 3M sodium acetate and 2.5 volumes of absolute ethanol. The digested DNA was collected by centrifugation, the supernatant was removed and the DNA dried and resuspended in water.

B. Preparation of the TLB Linker

The following single stranded DNA segments are conventionally synthesized by methods well known in the art on an automated DNA synthesizer (Model 380B Applied Biosystems 850 Lincoln Center Drive, Foster City Calif. 94404) using β-cyanoethyl phosphoramidite chemistry.

BGT3 (SEQ. ID. NO: 19)
5'-GATCCGCCAC CATGGATGCA ATGAAGAGAG GGCTCTGCTG TGTGCTGCTG CTGTGTGGAG CAGTCTTCGT TTCGCCCAGC CAGGAAATCC ATGCCCGATT CAGAATCCGC AAAA-3'

BGT4 (SEQ. ID. NO: 20)
5'-GATCTTTTGC GGATTCTGAA TCGGGCATGG ATTTCCTGGC TGGGCGAAAC GAAGACTGCT CCACACAGC AGCAGCACAC AGCAGAGCCC TCTCTTCATT GCATCCATGG TGGCG-3'.

BGT3 and BGT4 are complementary DNA molecules. The synthetic DNA segments were dissolved in 50 μl of TE buffer (TE is 10 mM Tris-HCl (pH 7.4) and 1 mM ethylenediaminetetraacetic acid (EDTA)) and stored at 0° C.

The DNA strands were annealed as follows. Fifty pmoles each of BGT3 and BGT4 were mixed and heated to 95° C. for fifteen minutes. The mixture was slowly brought to room temperature allowing the two complementary strands to anneal and form the double stranded DNA linker known as TLB (SEQ. ID. NO: 21).

C. Final Construction of pLP53-TLB

The DNA prepared in Example 1A was ligated with TLB (SEQ. ID. NO: 21). One μl of the DNA from Example 1A and 1 μl of TLB were ligated in a reaction that contained 1 μl (10 units) of T4 DNA ligase, 66 mM Tris-HCl (pH 7.6), 6.6 mM $MgCl_2$, 10 mM dithiothreitol (DTT) and 66 mM adenosine 5'-triphosphate (ATP) in a total volume of 10 μl. The mixture was incubated at 4° C. for 16 hours. The ligation mix was used to transform *Escherichia coli* K12 AG1 cells as described below.

D. Transformation Procedure

Frozen competent *Escherichia coli* K12 AG1 cells are obtained from Stratagene, 3770 Tansey Road, San Diego, Calif. 92121. About 5 μl of the ligation reaction is mixed with a 100 μl aliquot of competent cells and then the cell-DNA mixture is incubated on ice for one hour, heat-shocked at 42° C. for 45 seconds, then chilled on ice for about 2 minutes. The cell-DNA mixture is diluted into 1 ml of SOC media (2% tryptone, 0.05% yeast extract, 10 mM NaCl, 2.5 mM KCl, 10 mM each of $MgCl_2$ and $MgSO_4$, 20 mM glucose and distilled water) in Falcon 2059 tubes (Curtin Matheson, Chicago, Ill.) and incubated at 37° C. for one hour. About one hundred microliter aliquots are plated on LB-agar plates (1% tryptone, 0.5% yeast extract, 1% NaCl and 1.5% agar, pH 7.0) containing 100 μg/ml ampicillin and incubated at 37° C. until colonies appear.

Alternatively, cells can be made competent for transformation as follows. A 50 ml culture of *Escherichia coli* K12 AG1 cells is grown in L-broth (10 g tryptone, 10 g NaCl and 5 g yeast extract per liter of $H_2O$ and brought to pH 7.5) to an O.D. 590 of 0.5 absorbance units. The culture is chilled on ice for ten minutes and then the cells are collected by centrifugation. The cell pellet is resuspended in 25 ml of cold 50 mM $CaCl_2$:10 mM Tris-HCl (pH 8.0) and incubated on ice for 15 minutes. The cells are collected by centrifugation and the cell pellet is resuspended in 2.5 ml of cold 50 mM $CaCl_2$:10 mM Tris-HCl (pH 8.0). The sample can be held at 4° C. for 16 hours. The transformation of these competent cells is carried out as described above.

E. DNA Isolation

Following transformation, ampicillin resistant cells were picked and used to inoculate 2 mls of TY broth (1% tryptone, 0.5% yeast extract, 1% NaCl, pH 7.4) and 100 μg/ml ampicillin. These cultures were grown for 16 hours at 37° C. with aeration. Plasmid DNA was isolated from the cultures as follows. All of the following manipulations were done at ambient temperature unless otherwise indicated. One and a half ml of each of the cultures was transferred to a microcentrifuge tube. The cells were collected by a 1 minute centrifugation. The supernatant was removed with a fine-tip aspirator and the cell pellet was suspended in 100 μl of a solution containing 50 mM glucose, 10 mM EDTA and 25 mM Tris-HCl (pH 8.0). After incubation at room temperature for 5 minutes, 200 μl of an alkaline sodium dodecyl sulfate (SDS) solution (0.2N NaOH, 1% SDS) was added. The tube was gently inverted to mix and then maintained on ice for 5 minutes. Next, 150 μl of a potassium acetate solution (prepared by adding 11.5 ml of glacial acetic acid and 28.5 ml of water to 60 ml of 5M potassium acetate, resulting in a solution which is 3M with respect to potassium and 5M with respect to acetate) was added and the contents of the tube mixed by gently vortexing. The sample was kept on ice for 5 minutes and then centrifuged for 10 minutes. The supernatant was transferred to a second centrifuge tube to which an equal volume of a mixture of phenol (saturated with 0.1M Tris (pH 8.0)) and chloroform was added. The sample was mixed and then centrifuged for 5 minutes. The supernatant was collected. One ml of ice-cold absolute ethanol was added to the supernatant. The sample was mixed, held at room temperature for 5 minutes and then the DNA was collected by a 5 minute centrifugation. The supernatant was removed by aspiration and 500 μl of 70% ethanol was added to the DNA pellet. The sample was gently vortexed to wash the pellet and centrifuged for 2 minutes. The supernatant was removed and the DNA pellet was dried under vacuum. The DNA was dissolved in 50 μl of TE buffer and stored at 4° C. If greater amounts of the plasmid DNA are desired, the large scale isolation of plasmid DNA can be carried out by the method described by Maniatis et al., supra.

Figure 2:
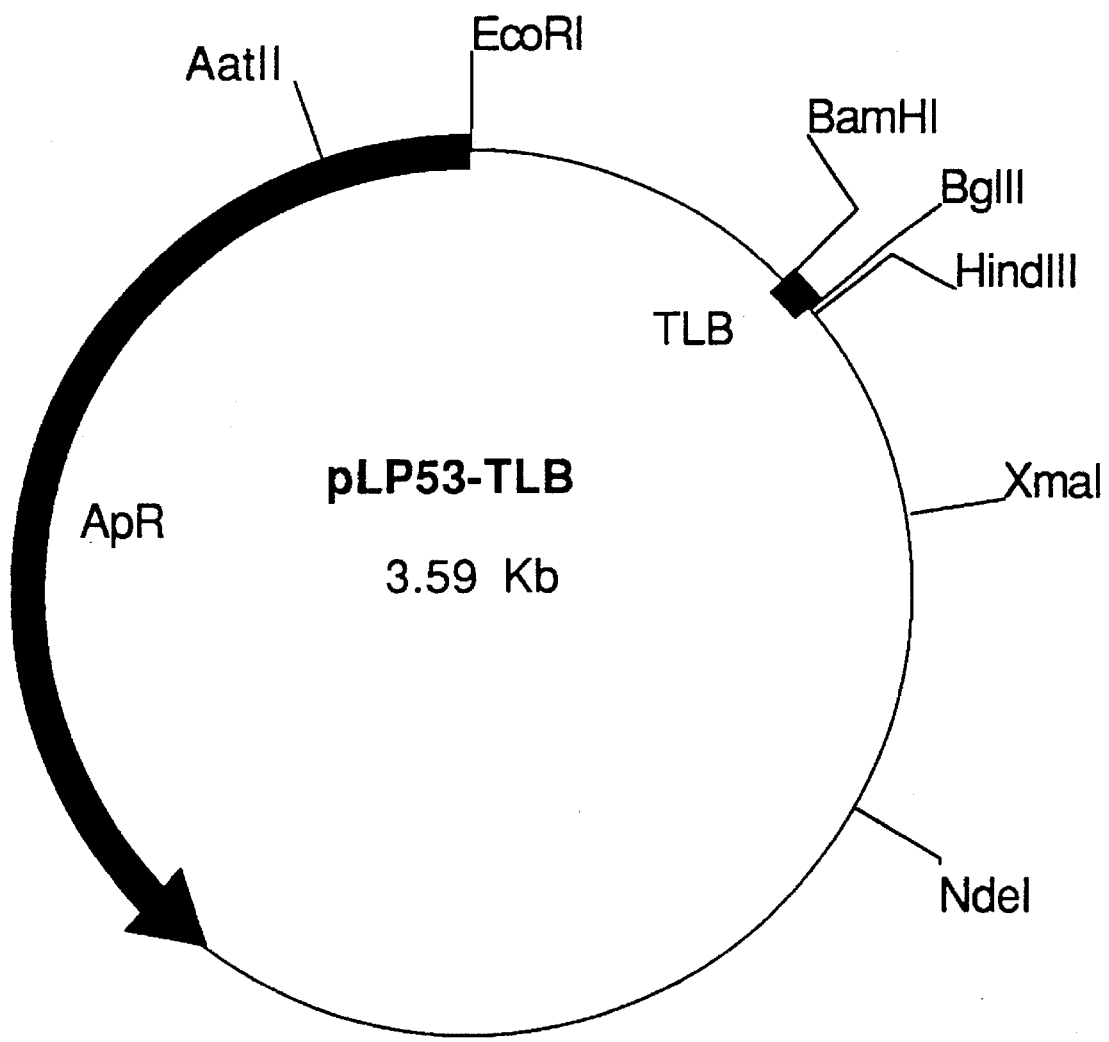
FIG. 2 is a restriction and function map of pLP53-TLB.

A restriction and function map of pLP53-TLB is shown in FIG. 2.

EXAMPLE 2

Construction of pmt6-hd

The following example provides a method for construction of plasmid pmt6-hd. Preferably, plasmid pmt6-hd is constructed by the methods described by Burck et al., supra.

A. Construction of Intermediate Plasmid pTPA103

Figure 3:
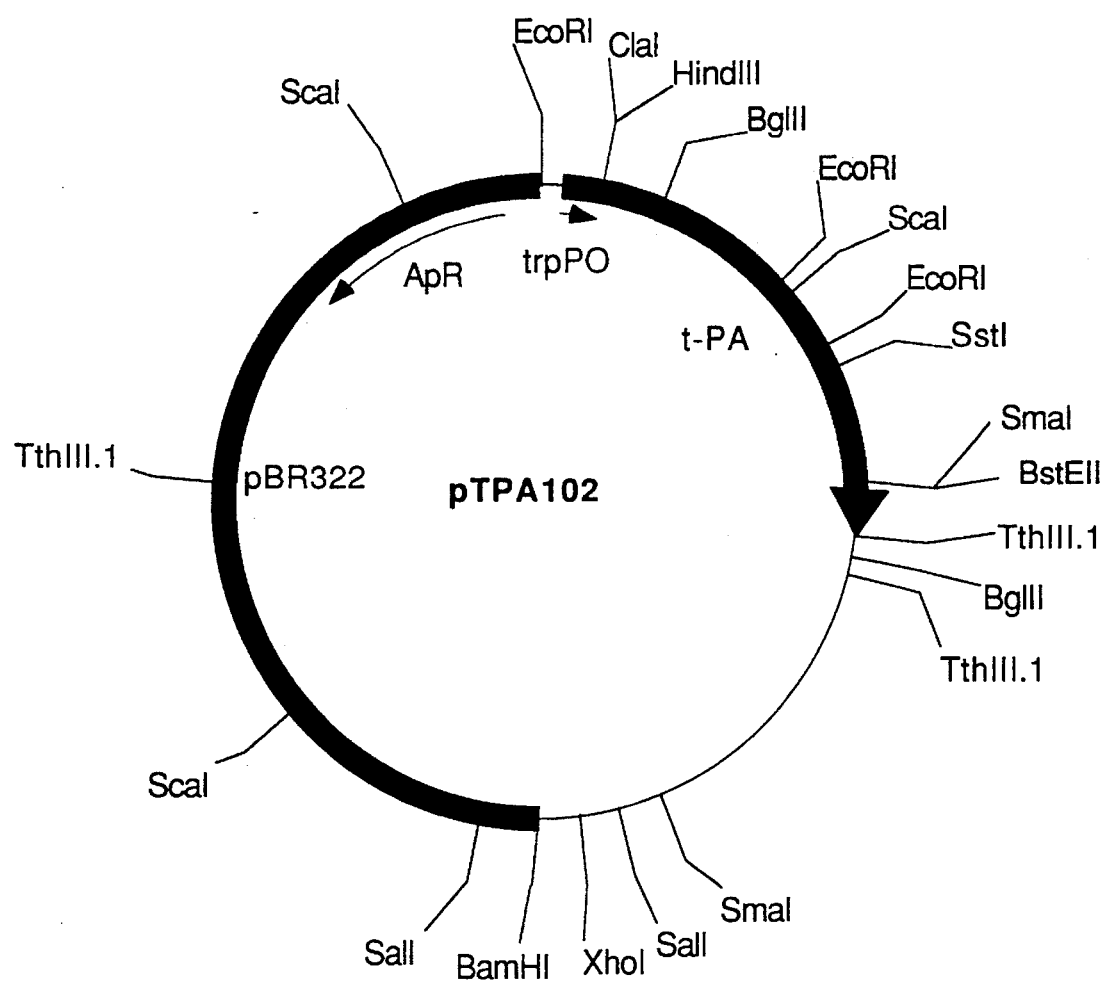
FIG. 3 is a restriction and function map of pTPA102.

Plasmid pTPA102 comprises the DNA coding sequence of human tissue plasminogen activator. Plasmid pTPA102 can be isolated from *Escherichia coli* K12 MM294/pTPA102, a strain available from the Northern Regional Research Laboratory under the accession number NRRL B-15834. A restriction site and function map of plasmid pTPA102 is presented in FIG. 3 of the accompanying drawings. Plasmid pTPA102 DNA is isolated from *E. coli*

K12 MM294/pTPA102 in substantial accordance with the procedure of Example 1E.

Fifty μg of plasmid pTPA102 (in about 50 μl of TE buffer) was added to 10 μl of 10× TthlllI buffer (0.5M NaCl, 80 mM Tris-HCl (pH 7.4), 80 mM MgCl₂, 80 mM 2-mercaptoethanol and 1 mg/ml BSA (bovine serum albumin) and 80 μl of H₂O. Ten μl (50 units) of restriction enzyme TthlllI was added to the solution of DNA, and the resulting reaction mixture was incubated at 65° C. for 2 hours. Following the incubation period, loading buffer was added to the sample (final concentration of loading buffer was 2.5% v/v glycerol, 0.005% w/v bromphenol blue, and 0.05% v/v xylene cyanole). The sample was fractionated by gel electrophoresis through an agarose gel. Following electrophoresis, the gel was stained with a dilute solution of ethidium bromide. The digested DNA was visualized under a 300 nm UV light, and the ~4.4 kilobase pair (kb) TthlllI restriction fragment that comprises the t-PA coding sequence was isolated from the gel. Methods for preparative gel electrophoresis are known in the art. A number of these methods are described by Maniatis et al., supra. and are useful in carrying out the above procedures. About 10 μg of the desired ~4.4 kb TthlllI restriction fragment was obtained and dissolved in 10 μl of TE buffer.

About 5 μl of 10× Klenow buffer (500 mM potassium phosphate (pH 7.5) 30 mM MgCl₂ and 10 mM 2-mercaptoethanol) and 30 μl of H₂O were added to the solution comprising the ~4.4 kb TthlllI restriction fragment, and after the further addition of about 5 μl of Klenow enzyme (~5 units), the reaction mixture was incubated at 16° C. for 30 minutes. After the Klenow reaction, the DNA was precipitated with ethanol and resuspended in 3 μl of 10× ligase buffer (660 mM Tris-HCl (pH 7.6), 66 mM MgCl₂, 100 mM DTT, and 10 mM ATP) and 14 μl of H₂O.

BamHI linkers (available from N.E.B.) which had the following sequence:

were kinased and prepared for ligation by the following procedure. Four μl of the BamHI linkers (~2 μg) were dissolved in about 20 μl of H₂O and 5 μl of 10× kinase buffer (500 mM Tris-HCl (pH 7.6) and 100 mM MgCl₂), incubated at 90° C. for two minutes, and then cooled to room temperature. Five μl of g-³²P-ATP (~20 μCi), 2.5 μl of 1M DTT, and 5 μl of polynucleotide kinase (~10 units) were added to the mixture, which was then incubated at 37° C. for 30 minutes. Then, 3.35 μl of 0.01M ATP and 5 μl of kinase were added, and the reaction was continued for another 30 minutes at 37° C. The radioactive ATP aids in determining whether the linkers have ligated to the target DNA.

About 10 μl of the kinased BamHI linkers were added to the solution of ~4.4 kb TthlllI restriction fragment, and after the addition of 2 μl of T4 DNA ligase (~1000 units) and 1 μl of T4 RNA ligase (~2 units), the ligation reaction was incubated overnight at 4° C. The ligated DNA was precipitated with ethanol and resuspended in 5 μl of 10× HindIII buffer (500 mM Tris-HCl (pH 8.0), 100 mM MgCl₂ and 500 mM NaCl) and 40 μl of H₂O. About 50 μl (~50 units) of restriction enzyme HindIII was added to the solution of DNA, and the resulting reaction was incubated at 37° C. for 2 hours.

The HindIII-digested DNA was extracted and then precipitated with ethanol and collected as described in Example 1A, and resuspended in 10 μl of 10× BamHI buffer (500 mM Tris-HCl (pH 8.0), 100 mM MgCl₂, 1M NaCl) and 90 μl of H₂O. About 10 μl (100 units) of restriction enzyme BamHI was added to the solution of DNA, and the resulting reaction was incubated at 37° C. for 2 hours. After the BamHI digestion, the reaction mixture was loaded onto an agarose gel, and the ~2.0 kb BamHI-HindIII restriction fragment was isolated from the gel as described above. About 4 μg of the desired fragment were obtained and suspended in about 5 μl of TE buffer.

To construct plasmid pTPA103, the ~2.0 kb BamHI-HindIII restriction fragment derived from plasmid pTPA102 was inserted into BamHI-HindIII-digested plasmid pRC. Plasmic pRC was constructed by inserting an ~288 bp EcoRI-ClaI restriction fragment that comprises the promoter and operator (trpPO) sequences of the *Escherichia coli* trp operon into EcoRI-ClaI-digested plasmid pKC7. Plasmid pKC7 can be obtained from the American Type Culture Collection in *E. coli* K12 N100/pKC7 under the accession number ATCC 37084. The ~288 bp EcoRI-ClaI restriction fragment that comprises the trpPO can be isolated from plasmid pTPA102. Plasmid pKC7 and plasmid pTPA102 can be obtained from the aforementioned cell lines in substantial accordance with the procedure of Example 1E. This ~0.29 kb EcoRI-ClaI restriction fragment of plasmid pTPA102 comprises the transcription activating sequence and most of the translation activating sequence of the *Escherichia coli* gene and has the sequence presented as SEQ. ID. NO: 22.

Thus, to construct plasmid pRC, about 2 μg of plasmid pKC7 in 10 μl of TE buffer were added to 2 μl of 10× ClaI buffer (0.5M NaCl, 60 mM Tris-HCl (pH 7.9), 60 mM MgCl₂, and 1 mg/ml BSA) and 6 μl of H₂O. About 2 μl (~10 units) of restriction enzyme ClaI were added to the solution of plasmid pKC7 DNA, and the resulting reaction was incubated at 37° C. for 2 hours. The ClaI-digested plasmid pKC7 DNA was purified and collected by ethanol precipitation. The DNA was resuspended in 2 μl of 10× EcoRI buffer (500 mM Tris-HCl (pH 8.0), 100 mM MgCl₂ and 1M NaCl) and 16 μl of H₂O. About 2 μl (~10 units) of restriction enzyme EcoRI were added to the solution of ClaI-digested plasmid pKC7 DNA, and the resulting reaction was incubated at 37° C. for 2 hours. The EcoRI-ClaI-digested plasmid pKC7 DNA was extracted, precipitated with ethanol and resuspended in 3 μl of 10× ligase buffer and 20 μl of H₂O.

About 20 μg of plasmid pTPA102 in about 20 μl of TE buffer were added to 10 μl of 10× ClaI buffer and 60 μl of H₂O. About 10 μl (50 units) of restriction enzyme ClaI were added to the solution of plasmid pTPA102 DNA, and the resulting reaction was incubated at 37° C. for 2 hours. The ClaI-digested plasmid pTPA102 DNA was precipitated with ethanol and resuspended in 10 μl of 10× EcoRI buffer and 80 μl of H₂O. About 10 μl (~50 units) of restriction enzyme EcoRI was added to the solution of ClaI-digested plasmid pTPA102 DNA, and the resulting reaction was incubated at 37° C. for 2 hours.

The EcoRI-ClaI-digested plasmid pTPA102 DNA was extracted once with phenol, loaded onto a 7% polyacrylamide gel, and electrophoresed until the ~288 base pair EcoRI-ClaI restriction fragment that comprises the trpPO was separated from the other digestion products. The ~288 bp EcoRI-ClaI restriction fragment was isolated from the gel (methods for preparative acrylamide gel electrophoresis are described by Maniatis et al., supra), about 1 μg of the desired fragment was obtained, suspended in 5 μl of TE buffer, and added to the solution of EcoRI-ClaI-digested plasmid pKC7 DNA prepared as described above. About 2 μl (1000 units) of T4 DNA ligase was then added to the mixture of DNA, and the resulting ligation reaction was incubated at 16° C. for 2 hours. The ligated DNA constituted the desired plasmid pRC DNA.

The ligated DNA was used to transform *Escherichia coli* K12 HB101 competent cells (available from BRL) in substantial accordance with the procedure of Example 1D. The transformed cells were plated on L agar containing 100 μg/ml ampicillin, and the ampicillin-resistant transformants were screened by restriction enzyme analysis of their plasmid DNA to identify the desired *E. coli* K12 HB101/pRC colonies. Plasmid pRC DNA was obtained from the *E. coli* K12 HB101/pRC transformants in substantial accordance with the procedure of Example 1E.

About 2 μg of plasmid pRC DNA in 2 μl of TE buffer were added to 2 μl of 10× HindIII buffer and 16 μl of H$_2$O. About 2 μl (10 units) of restriction enzyme HindIII were added to the solution of plasmid pRC DNA, and the resulting reaction incubated at 37° C. for two hours. The HindIII-digested plasmid pRC DNA was extracted once with phenol and then twice with chloroform, precipitated with ethanol, resuspended in 2 μl of 10× BamHI buffer and 16 μl of H$_2$O. About 2 μl (~10 units) of restriction enzyme BamHI were added to the solution of HindIII-digested plasmid pRC DNA, and the resulting reaction was incubated at 37° C. for 2 hours.

The BamHI-HindIII-digested plasmid DNA was extracted once with phenol and then twice with chloroform. The DNA was precipitated with ethanol and resuspended in 3 μl of 10× ligase buffer and 20 μl of H$_2$O. The ~4 μg (in ~5 μl of TE buffer) of ~2.0 kb HindIII-BamHI restriction fragment of plasmid pTPA102 were then added to the solution of BamHI-HindIII digested plasmid pRC DNA. About 2 μl (1000 units) of T4 DNA ligase were added to the mixture of DNA, and the resulting reaction was incubated at 16° C. for 2 hours. The ligated DNA constituted the desired plasmid pTPA103 DNA.

To reduce undesired transformants, the ligated DNA was digested with restriction enzyme NcoI, which cuts plasmid pRC but not plasmid pTPA103. Thus, digestion of the ligated DNA with NcoI reduces undesired transformants, because linearized DNA transforms *Escherichia coli* at a lower frequency than closed, circular DNA. To digest the ligated DNA, the DNA was first precipitated with ethanol and then resuspended in 2 μl of 10× NcoI buffer (1.5M NaCl, 60 mM Tris-HCl (pH 7.8), 60 mM MgCl$_2$, and 1 mg/ml BSA) and 16 μl of H$_2$O. About 2 μl (10 units) of restriction enzyme NcoI were added to the solution of DNA, and the resulting reaction was incubated at 37° C. for 2 hours.

Figure 4:
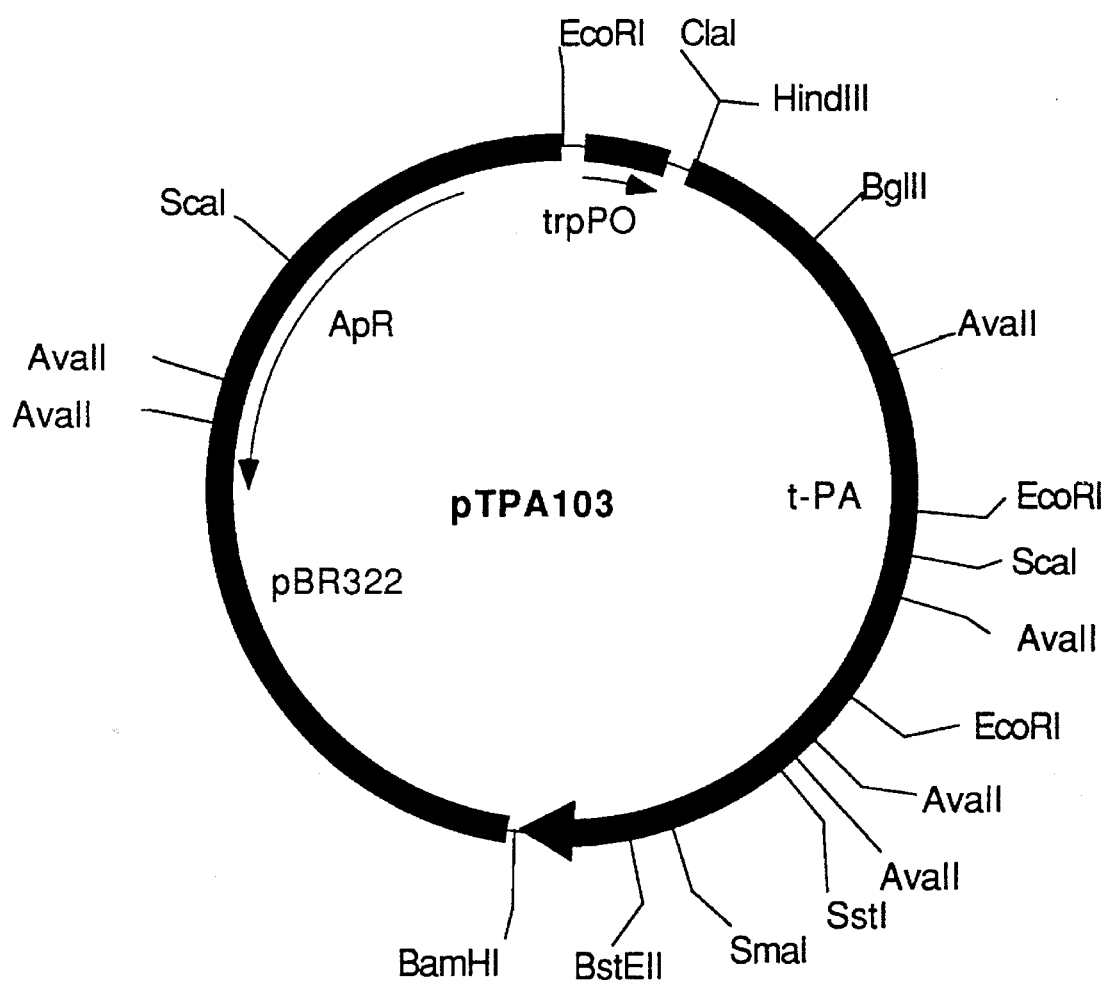
FIG. 4 is a restriction and function map of pTPA103.

The ligated and then NcoI-digested DNA sample was used to transform *Escherichia coli* K12 RV308 (NRRL B-15624). *E. coli* K12 RV308 cells were made competent and transformed in substantial accordance with the procedure of Example 1D. The transformation mixture was plated on L agar containing 100 μg/ml ampicillin. The ampicillin-resistant transformants were tested for sensitivity to kanamycin, for though plasmid pRC confers kanamycin resistance, plasmid pTPA103 does not. The ampicillin-resistant, kanamycin-sensitive transformants were then used to prepare plasmid DNA, and the plasmid DNA was examined by restriction enzyme analysis to identify the *E. coli* K12 RV308/pTPA103 transformants. A restriction site and function map of plasmid pTPA103 is presented in FIG. 4 of the accompanying drawings. Plasmid pTPA103 DNA was isolated from the *E. coli* K12 RV308/pTPA103 cells in substantial accordance with the procedure of Example 1E.

B. Construction of Intermediate Plasmid pTPA602

About 50 μg of plasmid pTPA103 in 45 μl of glass-distilled H$_2$O was added to 30 μl of 10× EcoRI buffer and 225 μl of H$_2$O. About 10 μl (80 units) of restriction enzyme EcoRI were added to the solution of plasmid pTPA103 DNA, and the mixture was incubated at 37° C. for 90 minutes. The EcoRI-digested plasmid pTPA103 DNA was precipitated with ethanol, resuspended in 50 μl of 1× loading buffer (10% glycerol and 0.02% bromophenol blue), loaded onto an agarose gel, and electrophoreses until the ~1.1 kb EcoRI restriction fragment was separated from the other reaction products. The ~1.1 kb EcoRI restriction fragment that comprises the t-PA amino-terminal-encoding DNA was isolated from the gel and resuspended in 160 μl of H$_2$O.

About 40 μl of 10× HgaI buffer (0.5M NaCl, 60 mM Tris-HCl (pH 7.4) and 0.1M MgCl$_2$), 200 μl of glass-distilled H$_2$O, and 20 μl (about 10 units) of restriction enzyme HgaI were added to the solution of ~1.1 kb EcoRI restriction fragment, and the resulting reaction was incubated at 37° C. for 4 hours. The HgaI-digested DNA was precipitated with ethanol and then electrophoresed on a 5% acrylamide gel, and the ~520 base pair restriction fragment that encodes the amino terminus of t-PA was isolated from the gel. About 5 μg of the ~520 bp HgaI fragment was obtained and suspended in 50 μl of H$_2$O.

About 12.5 μl of 10× Klenow buffer (0.5M Tris-HCl (pH 7.4), and 0.1M MgCl$_2$), 2 μl of a solution that was 6.25 mM in each of the four deoxynucleotide triphosphates, 2 μl of 0.2M DTT, 1 μl of 7 μg/ml BSA, 57.5 μl of glass-distilled H$_2$O, and 2 μl (10 units) of Klenow enzyme were added to the solution of the ~520 bp HgaI restriction fragment, and the resulting reaction was incubated at 20° C. for 30 minutes. The Klenow-treated DNA was incubated at 70° C. for 15 minutes and precipitated with ethanol.

About 500 picomoles of BamHI linker were phosphorylated using polynucleotide kinase in a total reaction volume of 25 μl. The reaction was carried out in substantial accordance with the procedure described in Example 2A. The kinased BamHI linkers were added to the solution of Klenow-treated, ~520 bp HgaI restriction fragment together with 15 μl of 10× ligase buffer, 7 μl (~7 Weiss units) of T4 DNA ligase, and enough glass-distilled H$_2$O to bring the reaction volume to 150 μl. The resulting reaction was incubated at 16° C. overnight.

The ligation reaction was heat-inactivated, and the DNA was precipitated with ethanol and resuspended in 5 μl of 10× BamHI buffer and 45 μl of H$_2$O. About 1 μl (16 units) of restriction enzyme BamHI was added to the solution of DNA, and the resulting reaction was incubated at 37° C. for 90 minutes. Then, another 16 units of BamHI enzyme were added to the reaction mixture, and the reaction was incubated at 37° C. for another 90 minutes. The reaction mixture was then electrophoresed on a 5% polyacrylamide gel, and the ~530 bp HgaI restriction fragment, now with BamHI ends, was purified from the gel. About 2 μg of the desired fragment was obtained and suspended in 20 μl of H$_2$O.

Figure 5:
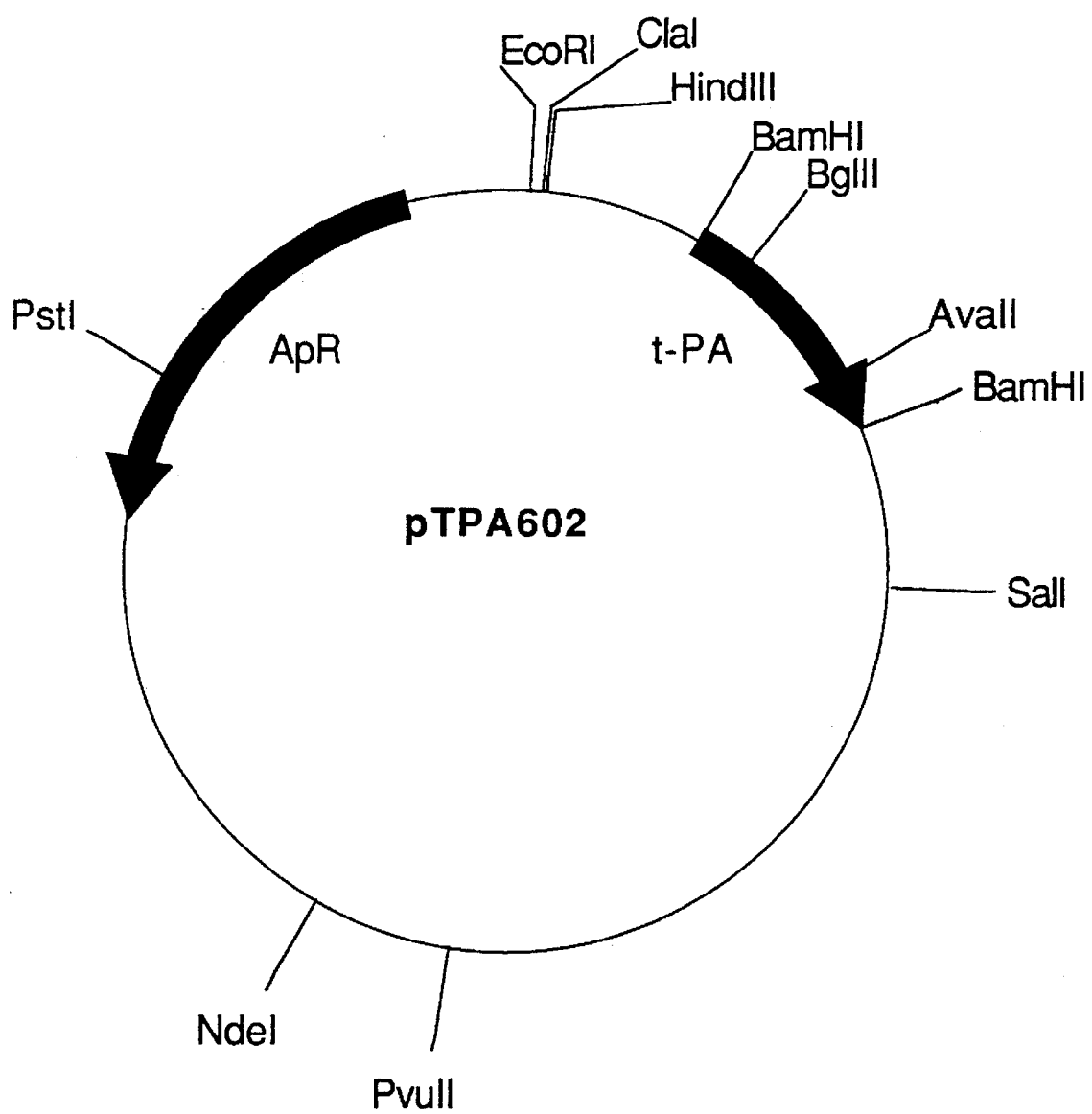
FIG. 5 is a restriction and function map of pTPA602.

BamHI-digested, dephosphorylated plasmid pBR322 DNA can be obtained from New England Biolabs. About 0.1 μg of BamHI-digested, dephosphorylated plasmid pBR322 in 2 μl of H$_2$O was added to 1 μl of the ~530 bp HgaI restriction fragment (with BamHI ends) of plasmid pTPA103, 14 μl of H$_2$O, 2 μl of 10× T4 DNA ligase buffer, and 1 μl (1 Weiss unit) of T4 DNA ligase, and the resulting reaction was incubated at 16° C. overnight. The ligated DNA constituted the desired plasmid pTPA602 and an equivalent plasmid designated pTPA601, which differs from plasmid pTPA602 only with respect to the orientation of the inserted, ~530 base pair restriction fragment. A restriction site and function map of plasmid pTPA602 is presented in FIG. 5 of the accompanying drawings.

The ligated DNA was used to transform *Escherichia coli* K12 MM294 (NRRL B-15625) in substantial accordance with the procedure of Example 1D. The transformed cells were plated on L agar containing ampicillin, and the ampicillin-resistant *E. coli* K12 MM294/pTPA602 and *E. coli* K12 MM294/pTPA601 cells were identified by restriction enzyme analysis of their plasmid DNA. Presence of an ~530 bp BamHI restriction fragment indicated that the plasmid was either pTPA602 or plasmid pTPA601.

C. Construction of Intermediate Plasmid pTPA603

About 5 μg of plasmid pTPA602 was dissolved in 20 μl of 10× BglII buffer (500 mM Tris-HCl (pH 8.0), 100 mM MgCl$_2$, 1M NaCl) and 180 μl of H$_2$O. About 3 μl (~24 units) of restriction enzyme BglII were added to the solution of plasmid pTPA602 DNA, and the resulting reaction was incubated at 37° C. for 90 minutes. Then, 13 μl of 10× BamHI buffer was added to the reaction mixture to bring the salt concentration of the reaction mixture up to that recommended for SalI digestion, and 2 μl (20 units) of restriction enzyme SalI was added to the reaction. The reaction was incubated at 37° C. for another 2 hours, then the DNA was precipitated with ethanol, resuspended in 75 μl of 1× loading buffer, loaded onto an agarose gel, and electrophoresed until the ~4.2 kb BglII-SalI restriction fragment was separated from the other digestion products. The region of the gel containing the ~4.2 kb BglII-SalI restriction fragment was excised from the gel, frozen, and the frozen segment was wrapped in plastic and squeezed to remove the ~4.2 kb fragment. The DNA was precipitated and resuspended in 20 μl of H$_2$O; about 200 nanograms of the desired fragment were obtained.

About 12 μg of plasmid pTPA103 was dissolved in 15 μl of 10× BglII buffer and 135 μl of H$_2$O. About 2 μl (16 units) of restriction enzyme BglII was added to the solution of plasmid pTPA103 DNA, and the resulting reaction was incubated at 37° C. for 90 minutes. About 10 μl of 10× BamHI buffer was added to the solution of BglII-digested plasmid pTPA103 DNA to bring the salt concentration of the reaction mixture up to that required for SalI digestion. Then, about 2 μl (20 units) of restriction enzyme SalI was added to the solution of BglII-digested plasmid pTPA103 DNA, and the reaction was incubated at 37° C. for another 90 minutes. The BglII-SalI digested plasmid pTPA103 DNA was concentrated by ethanol precipitation and then loaded onto an agarose gel, and the ~2.05 kb BglII-SalI restriction fragment that encodes all but the amino-terminus of t-PA was isolated from the gel, precipitated with ethanol and resuspended in 20 μl of H$_2$O. About 2 μg of the desired fragment was obtained.

Figure 6:
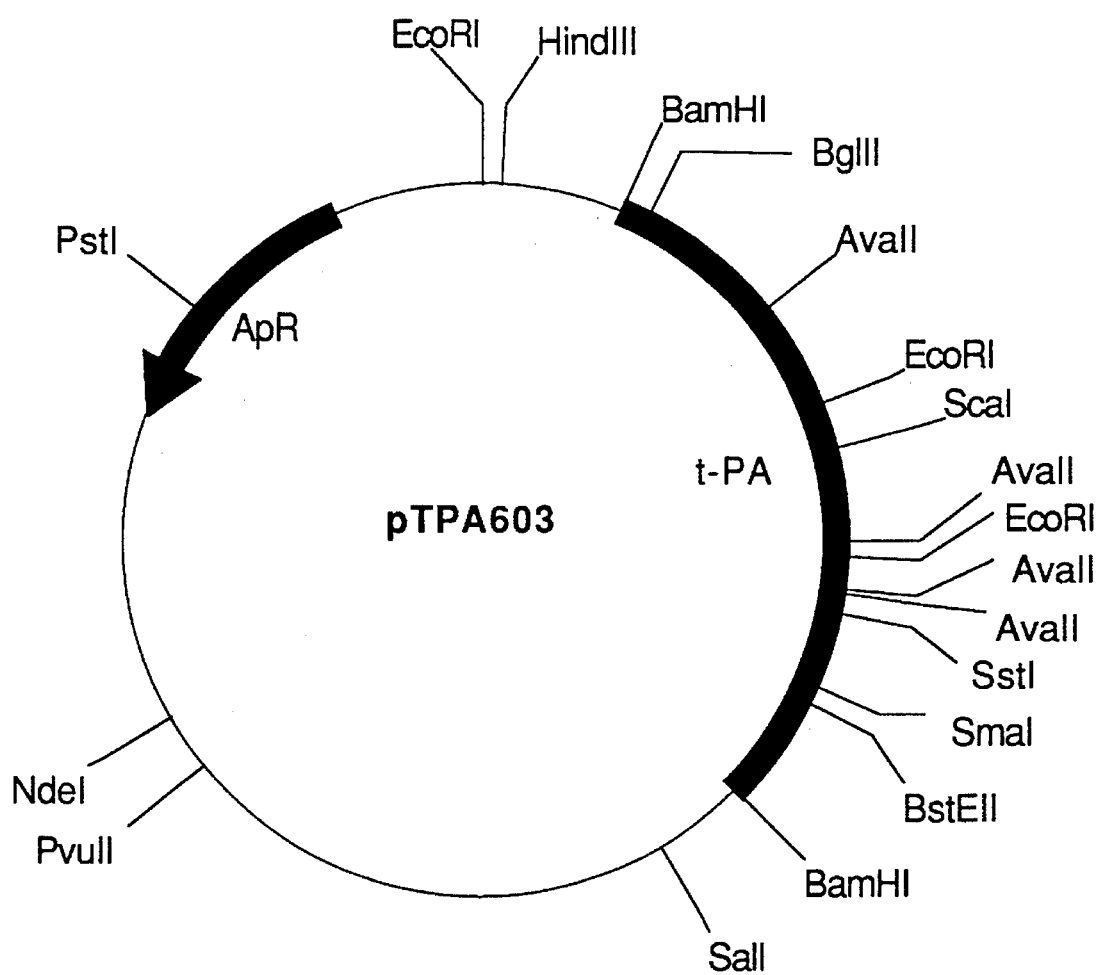
FIG. 6 is a restriction and function map of pTPA603.

About 5 μl of the ~4.2 kb BglII-SalI restriction fragment of plasmid pTPA602 and 2 μl of the ~2.05 kb BglII-SalI restriction fragment of plasmid pTPA103 were added to 2 μl of 10× ligase buffer, 10 μl of H$_2$O, and 1 μl (1 Weiss unit) of T4 DNA ligase, and the resulting ligation reaction was incubated at 16° C. overnight. The ligated DNA constituted the desired plasmid pTPA603. A restriction site and function map of plasmid pTPA603 is presented in FIG. 6 of the accompanying drawings.

The ligated DNA was used to transform *Escherichia coli* K12 MM294 in substantial accordance with the procedure of Example 1D. The transformed cells were plated on L agar containing ampicillin, and the ampicillin-resistant *E. coli* K12 MM294/pTPA603 transformants were identified by restriction enzyme analysis of their plasmid DNA.

D. Final Construction of Plasmid pmt6-hd

Site specific mutagenesis of the t-PA coding region and the construction of plasmid pmt6-hd is accomplished as follows. About 5 μg of plasmid pTPA103 in 10 μl of dH$_2$O are added to about 10 μl of 10× HindIII buffer and 80 μl of dH$_2$O. One μl (20 units) of restriction enzyme HindIII is added to the solution of plasmid pTPA103 DNA, and the resulting reaction mixture is incubated at 37° C. for 90 minutes. One μl (20 units) of restriction enzyme SstI and 10 μl of 1M Tris-HCl (pH 7.6) is added to the solution of HindIII-digested plasmid pTPA103 DNA, and the resulting mixture is incubated at 37° C. for 90 minutes. The 1.4 kb HindIII-SstI restriction fragment is isolated by preparative gel electrophoresis.

About 4.5 μg of the replicative form (RF) of M13mp18 DNA (available from NEB) in 35 μl of dH$_2$O is added to 10 μl of 10× HindIII buffer and 55 μl of dH$_2$O. One μl (about 20 units) of restriction enzyme HindIII is added to the solution of M13mp18 DNA, and the resulting reaction was incubated at 37° C. for 1 hour. One μl (about 20 units) of restriction enzyme SstI and 10 μl of 1M Tris-HCl (pH 7.6) is added to the solution of HindIII-digested M13mp18 DNA, and the resulting reaction is incubated at 37° C. for 1 hour. The large HindIII-SstI restriction fragment of M13mp18 is obtained by preparative gel electrophoresis and suspended in 20 μl of dH$_2$O. About 2 μl of the large HindIII-SstI restriction fragment of M13mp18, 2 μl of 10× T$_4$ DNA ligase buffer, 12 μl of dH$_2$O and 1 μl (1 Weiss unit) of T4 DNA ligase is added to 3 μl of the ~1.4 kb HindIII-SstI restriction fragment of plasmid pTPA103, and the resulting ligation reaction is incubated at 16° C. overnight.

*Escherichia coli* JM103 cells are made competent and transfected with the ligation mix in substantial accordance with the procedure described in the BRL M13 Cloning/ 'Dideoxy' Sequencing Instruction Manual, except that the amount of DNA used per transfection is varied (host cells other than JM103 may be used in this procedure. For examples of appropriate host cells, see Maniatis et al., 1989, vol. 1 at pp. 414–415). This method is also described by Maniatis et al., supra., at 1:4.37. Recombinant plaques are identified by insertional inactivation of the β-galactosidase a-fragment-encoding gene, which results in the loss of the ability to cleave X-Gal (5-bromo-4-chloro-3-indolyl-β-D-galactopyranoside) to its indigo colored cleavage product. For screening purposes, several white plaques are picked into 2.5 ml of L broth, to which is added 0.4 ml of *E. coli* K12 JM103 in logarithmic growth phase, that are cultured in minimal media stock to insure retention of the F episome that carries proAB. The 2.5 ml plaque-containing cell suspensions are incubated in an air-shaker at 37° C. for 8 hours. Cells from 1.5 ml aliquots are pelleted and RF DNA isolated in substantial accordance with the procedure of Example 1E. The remainder of each culture is stored at 4° C. for stock. The desired phage, designated MP18BW47, contains the ~1.4 kb HindIII-SstI restriction fragment of plasmid pTPA103 ligated to the ~7.2 kb EcoRI-HindIII restriction fragment of M13mp18.

About fifty ml of log phase *Escherichia coli* JM103 are infected with MP18BW47 and incubated in an air-shaker at 37° C. for 18 hours. The infected cells are pelleted by low speed centrifugation, and single-stranded MP18BW47 DNA is prepared from the culture supernatant by scaling up the procedure given in the Instruction Manual. Single-stranded MP18BW47 is mutagenized in substantial accordance with the teaching of Adelman, et al., 1983, DNA 2(3): 183–193, except that the Klenow reaction is done at room temperature for 30 minutes, then at 37° C. for 60 minutes, then at 10° C. for 18 hours. In addition, the S1 treatment is done at 20° C., the salt concentration of the buffer is one-half that recommended by the manufacturer, and the M13 sequencing primer (BRL) is used. The synthetic oligodeoxyribonucleotide primer used to delete the coding sequence for amino acid residues 4 through 175 of t-PA is:

5'-GGAGCCAGAT CTTACCAAGG AAACAGTGAC
TGCTAC-3' (SEQ D NO: 23).

The resulting mutagenesis mix is used to transfect *Escherichia coli* K12 JM103 is substantial accordance with the infection procedure described above. Desired mutants are identified by restriction enzyme analysis of RF DNA and by Maxam and Gilbert DNA sequencing (Maxam, A. M. and Gilbert, W. 1980, Proc. Natl. Acad. Sci. U.S.A. 74:560). The desired mutant, which has the coding sequence for amino acid residues 4 through 175 of t-PA deleted, was designated MP18BW52.

Plasmid pmt6-hd was constructed as follows. First, the plasmid pTPA603 was digested to completion with BamHI in accordance with the methods described above, and the ~1.9 kb BamHI fragment was isolated by preparative gel electrophoresis. Next, plasmid pAc373 (Miyamoto et al., 1985, *Mol. Cell. Biol.* 5:2860–2865) was digested with BamHI, extracted and ethanol precipitated. The BamHI digested pAc373 DNA was ligated with the ~1.9 kb BamHI fragment from plasmid pTPA603 to create intermediate plasmid pL100. Plasmid pAc373 was used because of the presence of convenient cloning sites in this plasmid. Other plasmids can be used instead of plasmid pAc373 to create plasmid pL100. Examples of such plasmids include pBR322, pUC18, and pUC19, all of which are publicly available. The ligated DNA was used to transform *Escherichia coli* K12 MM294 in substantial accordance with the procedure of Example 1D. The transformed cells were plated on L agar containing ampicillin, and the ampicillin-resistant *E. coli* K12 MM294/pL100 transformants were identified by restriction enzyme analysis of their plasmid DNA.

Plasmid pL100 DNA was digested to completion with restriction enzymes BglII and SstI and a 9.7 kb BglII-Sst fragment was isolated by preparative gel electrophoresis. MP18BW52 DNA, obtained as above, was digested with restriction enzymes BglII and SstI and an ~718 bp BglII-SstI fragment was isolated by preparative gel electrophoresis. This fragment was ligated with the 9.7 kb BglII-SstI fragment of plasmid pL100 in accordance with the method of Example 1C to create intermediate plasmid pL229. Plasmid pL229 was used to transform *Escherichia coli* K12 MM294 in substantial accordance with the procedure of Example 1D. The transformed cells were plated on L agar containing ampicillin, and the ampicillin-resistant *E. coli* K12 MM294/pL229 transformants were identified by restriction enzyme analysis of their plasmid DNA. Plasmid pL229 DNA was isolated as described in Example 1E and then digested with restriction enzyme BamHI. A ~1.4 kb BamHI fragment was isolated by preparative gel electrophoresis.

Figure 7:
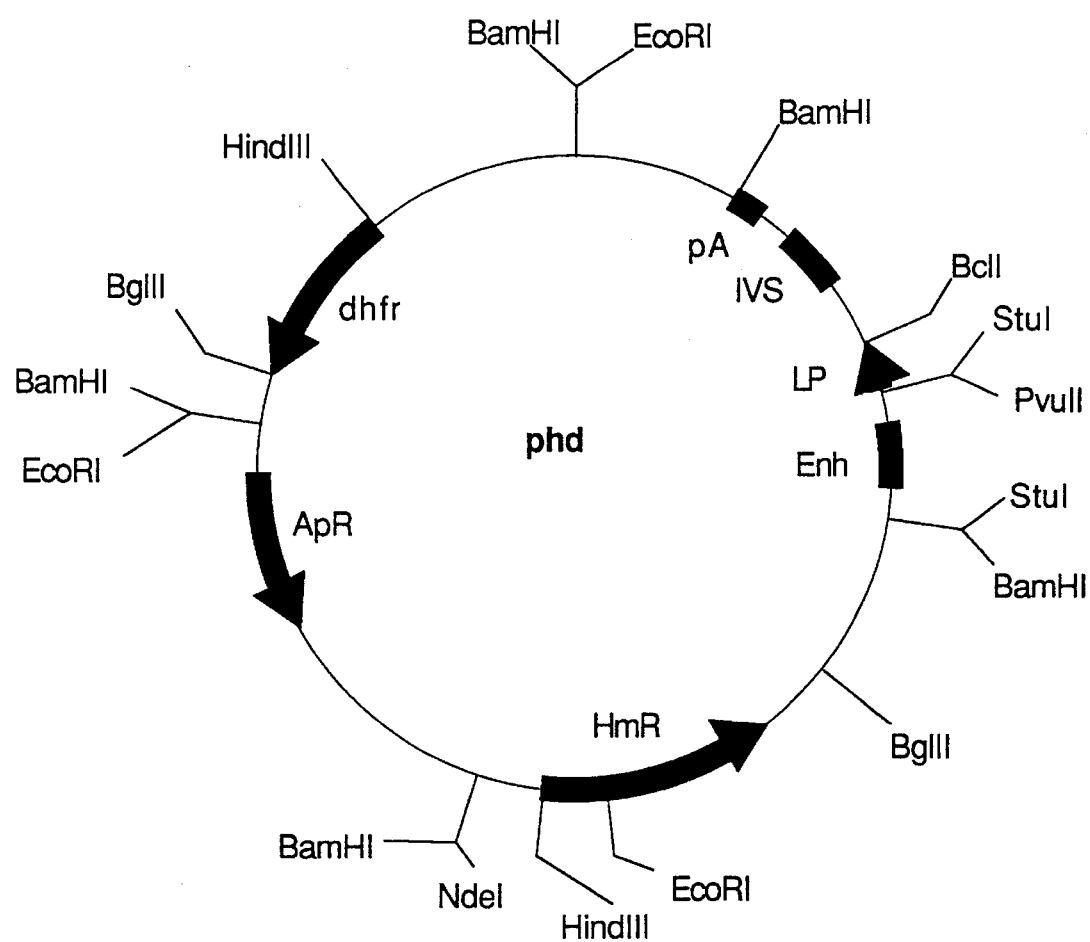
FIG. 7 is a restriction and function map of phd.
Figure 8:
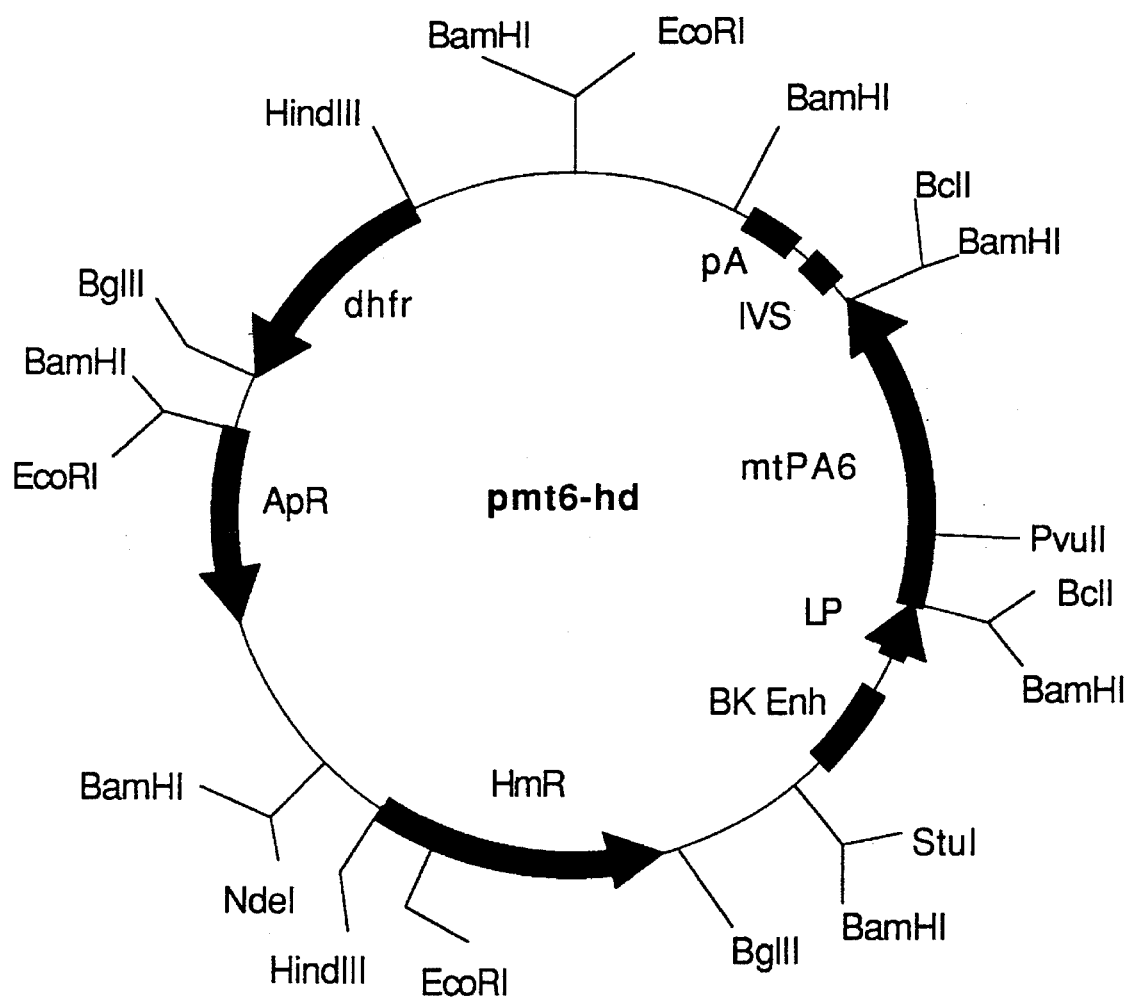
FIG. 8 is a restriction and function map of pmt6-hd.

*Escherichia coli* K12 GM48/phd cells are obtained in lyophil form from the Northern Regional Research Laboratory under accession number NRRL B-18525. The lyophilized cells are plated on L-agar plates containing 100 μg/ml ampicillin and incubated at 37° C. to obtain single colony isolates. Plasmid DNA can be isolated from these cells by the method described in Example 1E. A restriction and function map of plasmid phd is presented in FIG. 7. Plasmid phd was digested with BclI, purified and collected by ethanol precipitation. The BclI digested phd DNA was ligated with the ~1.4 kb BamHI fragment of plasmid pL229 to create the desired plasmid pmt6-hd. The ligated DNA was used to transform *Escherichia coli* K12 MM294 in substantial accordance with the procedure of Example 1D. The transformed cells were plated on L agar containing ampicillin, and the ampicillin-resistant *E. coli* K12 MM294/pmt6-hd transformants were identified by restriction enzyme analysis of their plasmid DNA. A restriction and function map of pmt6-hd is shown in FIG. 8.

EXAMPLE 3

Construction of Plasmid pTZ-t6

A. Preparation of the 1.4 Kilobase Pair BamHI Restriction Fragment of Plasmid pLP229.

Fifty μl (50 μg) of plasmid pL229 DNA (prepared in Example 2) was digested to completion with 10 μl (100 units) of BamHI in a 100 μl reaction volume containing 50 mM Tris-HCl (pH 8.0), 10 mM $MgCl_2$ and 50 mM NaCl. The sample was incubated at 37° C. for 2 hours. Following incubation, loading buffer was added to the sample (final concentration of loading buffer was 2.5% v/v glycerol, 0.005% w/v bromphenol blue, and 0.05% v/v xylene cyanole). The sample was fractionated by gel electrophoresis through a 1% agarose gel. Following electrophoresis, the gel was stained with a dilute solution of ethidium bromide. The digested DNA was visualized under a 300 nm ultraviolet light, and the 1.4 kilobase pair BamHI restriction fragment that comprises the mt-PA6 coding sequence was isolated from the gel by the Prep-A-Gene purification kit (Bio-Rad Laboratories, 1414 Harbour Way South, Richmond Calif. 94804) according to the manufacturer's recommendations. Other methods for preparative gel electrophoresis are well known in the art and can be used in place of the technique described above.

B. Preparation of the 2860 Base Pair BamHI Restriction Fragment of Plasmid pTZ18U Twenty μl (2 μg) of plasmid pTZ18U (available from Bio-Rad Laboratories, Mutagene Phagemid in vitro Mutagenesis kit catalog number 170-3576) was digested to completion with 2 μl (20 units) of BamHI in a reaction volume of 50 μl under the conditions described in Example 3A. The sample was diluted to a 100 μl volume with TE buffer. Two μl (0.5 units) of calf intestinal alkaline phosphatase (Boehringer Mannheim, Indianapolis, Ind. 46250) was added and the sample was incubated at 37° C. for 30 minutes. Following incubation, the sample was extracted once with an equal volume of phenol, once with an equal volume of phenol:chloroform (50:50) and once with an equal volume of chloroform:isoamyl alcohol (24:1). The DNA was precipitated from the sample by addition of 1/10 volume of 3M sodium acetate and 2volumes of absolute ethanol. The DNA was collected by centrifugation, the supernatant was removed and the DNA was dried and resuspended in water.

C. Ligation and Transformation

Figure 9:
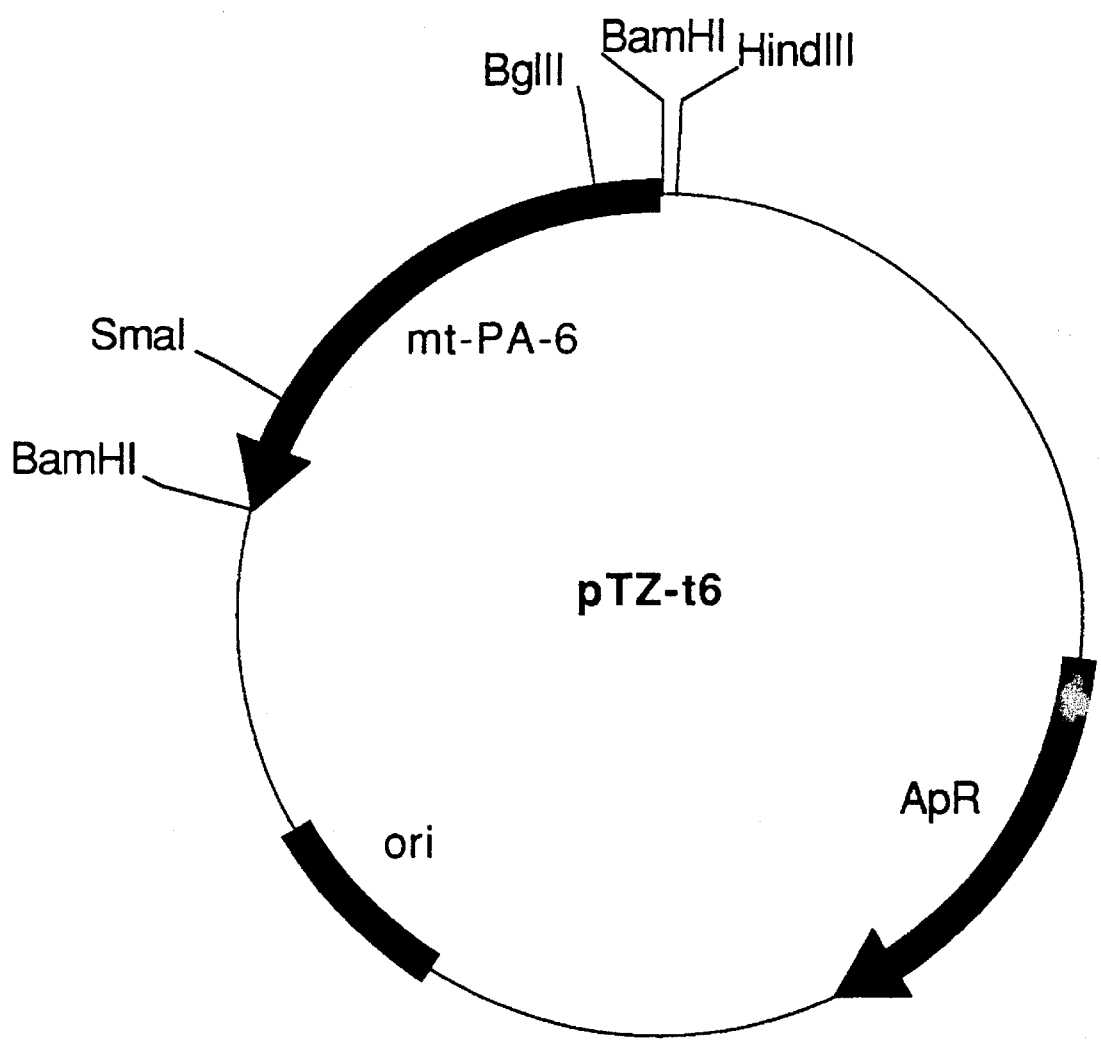
FIG. 9 is a restriction and function map of pTZ-t6.

One μl (0.05 μg) of the DNA prepared in Example 3A was ligated with one μl (0.01 μg) of the DNA prepared in Example 3B in a reaction that contained 1 μl (10 units) of T4 DNA ligase, 66 mM Tris-HCl (pH 7.6), 6.6 mM $MgCl_2$, 10 mM DTT and 66 mM adenosine 5'-triphosphate in a total volume of 10 μl. The mixture was incubated at 16° C. for 16 hours. The ligation mix was used to transform *Escherichia coli* K12 AG1 cells as described in Example 1D. The transformants were selected on TY agar plates containing 100 μg/ml of ampicillin grown overnight at 37° C. Plasmid DNA was isolated from the ampicillin resistant clones by the DNA isolation procedure of Example 1E. The ligation of these DNA fragments results in a mixture of two plasmids that contain the DNA fragment of Example 3A cloned into the DNA fragment of Example 3B in two orientations. The desired orientation, plasmid pTZ-t6, was determined by restriction enzyme analysis. Methods of restriction enzyme analysis are well known in the art. Maniatis et al., supra, present several of these methods. A restriction site and function map of pTZ-t6 is shown in FIG. 9.

EXAMPLE 4

Construction of Plasmid pTLB-t6D

A. Site-Specific Mutagenesis

Oligonucleotide site-specific mutagenesis was performed on plasmid pTZ-t6 DNA in accordance with the Muta-GeneR Phagemid in vitro Mutagenesis Instruction Manual (Bio-Rad Laboratories catalog number 170-3576). This procedure was utilized to mutate plasmid pTZ-t6 DNA in two steps. The first round of mutagenesis converted the amino acid at position 12 of the mt-PA-6 DNA encoded by plasmid pTZ-t6 from an asparagine to a glutamine. The mutagenic oligonucleotide used in this mutagenesis step had the DNA sequence (SEQ. ID. NO: 24):

5'-CAGTGACTGC TACTTTGGCC AGGGGTCAGC CTAC-CGTGGC-3'.

After each round of mutagenesis, the mutated DNA was analyzed by DNA sequencing as described in the Muta-GeneR Phagemid in vitro Mutagenesis Instruction Manual to confirm the success of the mutagenesis procedure.

The second round of mutagenesis inserted DNA encoding the amino acid glycine between amino acid positions 33 and 34 of mt-PA-6. The mutagenic oligonucleotide used in this mutagenesis step had the DNA sequence (SEQ. ID. NO: 25):

5'-GGGTGCCTCC TGCCTCCCAT GGAATGGGTC CATGATC-CTG ATAGGC-3'.

Figure 10:
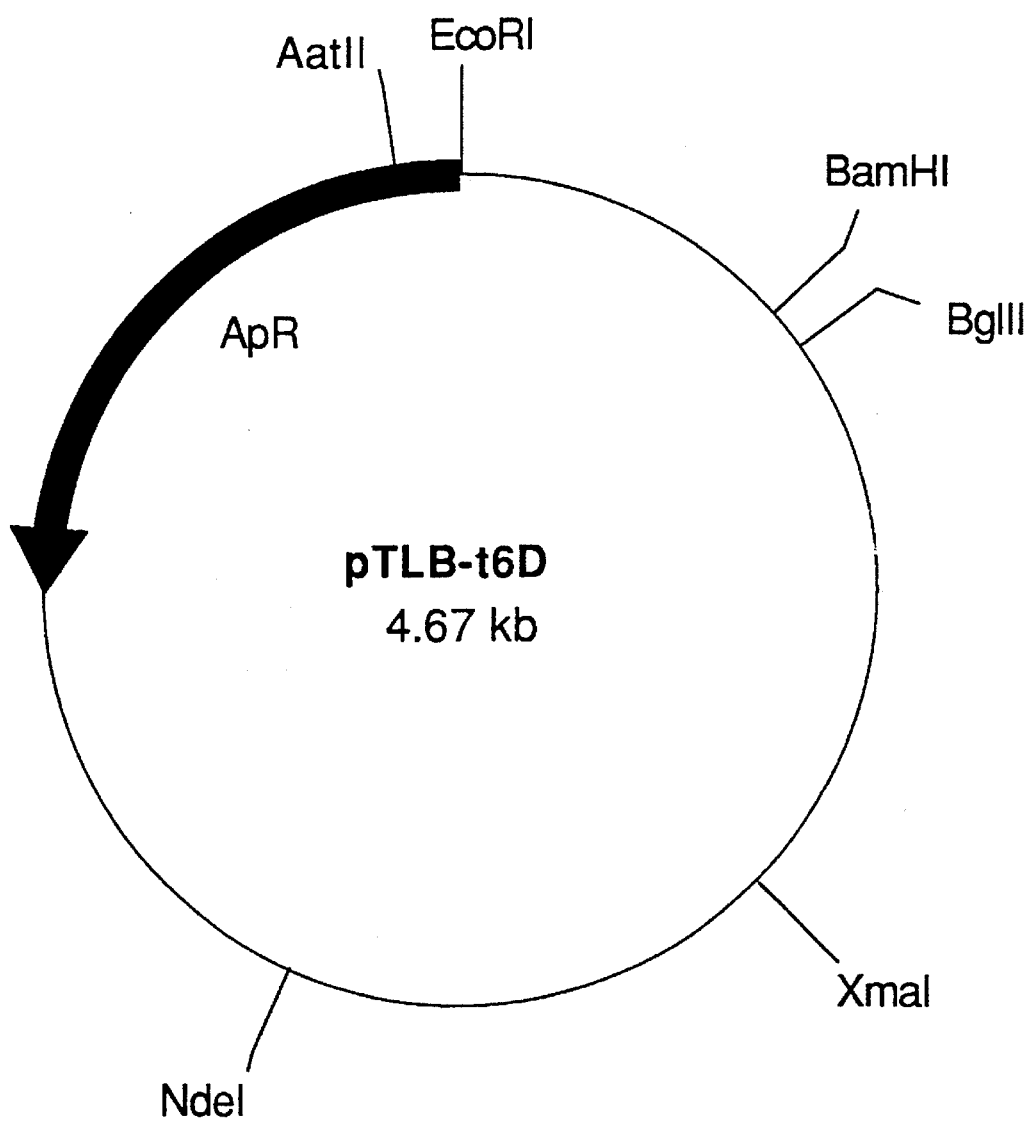
FIG. 10 is a restriction and function map of pTLB-t6D.

The mutated plasmid DNA was analyzed by DNA sequence analysis, and the resulting plasmid was called pTZ-t6D.
B. Preparation of the 1007 Base Pair XmaI-BglII Restriction Fragment of Plasmid pTZ-t6D About 50 µg of plasmid pTZ-t6D was digested to completion with 5 µl (50 units) of BglII and 25 µl (25 units) of XmaI in a 300 µl reaction volume containing 50 mM Tris-HCl (pH 8.0), 10 mM MgCl$_2$ and 50 mM NaCl. The sample was electrophoresed through a 1% agarose gel. The gel was stained with a dilute solution of ethidium bromide and the digested DNA was visualized under a 300 nm UV light. The portion of the gel that contained the 1007 base pair XmaI-BglII restriction fragment was excised from the gel and purified as described above.
C. Preparation of the 3273 Base Pair XmaI-BglII Restriction Fragment of Plasmid pLP53-TLB One µg of plasmid pLP53-TLB DNA (prepared in Example 1) was digested to completion with 1 µl (10 units) of BglII and 9 µl (9 units) of XmaI in a 200 µl reaction volume containing 50 mM Tris-HCl (pH 8.0), 10 mM MgCl$_2$, and 50 mM NaCl. The digested DNA was purified and the 3272 base pair restriction fragment was collected as described in Example 3B.
D. Ligation and Transformation One µl of the DNA prepared in Example 4B was ligated with one µl of the DNA prepared in Example 4C in a reaction volume of 10 µl that contained 1 µl (10 units) of T4 DNA ligase, 66 mM Tris-HCl (pH 7.6), 6.6 mM MgCl$_2$, 10 mM DTT and 66 mM adenosine 5'-triphosphate. The mixture was incubated at 16° C. for 16 hours. The ligation mixture was used to transform *Escherichia coli* K12 AG1 cells by the method described in Example 1D. The transformants were selected by overnight growth on TY agar plates containing 100 µg/ml of ampicillin. Plasmid DNA was isolated from the ampicillin resistant clones by the DNA isolation procedure of Example 1E. These DNA samples were screened by restriction enzyme analysis for the desired plasmid, pTLB-t6D. A restriction site and function map of pTLB-t6D is shown in FIG. 10.

EXAMPLE 5

Construction of Plasmid pTLB-t6E

A. Site Specific Mutagenesis

Oligonucleotide site-specific mutagenesis was performed on plasmid pTZ-t6 DNA as described in Example 4A. The first round of mutagenesis was identical to that described in Example 4A. However, the second round of mutagenesis converted the DNA encoding proline at amino acid position 48 of mt-PA-6 to a glycine. The mutagenic oligonucleotide used in this mutagenesis step had the DNA sequence (SEQ. ID. NO: 26):

5'-GGTTTACACA GCACAGAACG GCAGTGCACA GGCACTGGGC CTGGG C3'.

Figure 11:
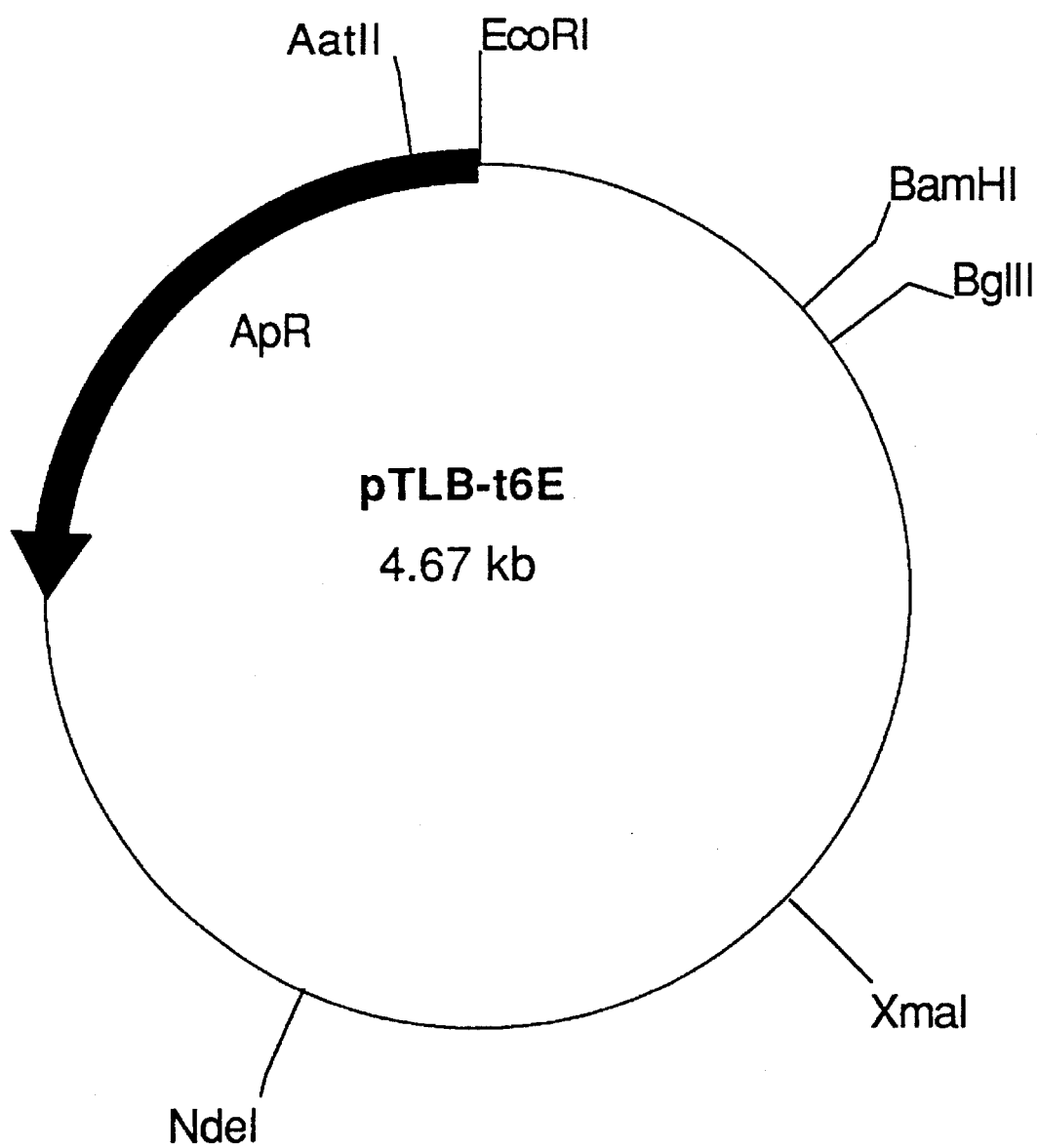
FIG. 11 is a restriction and function map of pTLB-t6E.

The mutated plasmid DNA was analyzed by DNA sequence analysis and the resulting plasmid was called pTZ-t6E.
B. Preparation of the 1007 Base Pair XmaI-BglII Restriction Fragment of Plasmid pTZ-t6E The 1007 base pair XmaI-BglII restriction fragment of plasmid pTZ-t6E was prepared in substantial accordance with the method described in Example 4B.
C. Preparation of the 3273 Base Pair XmaI-BglII Restriction Fragment of Plasmid pLP53TLB The 3273 base pair XmaI-BglII restriction fragment of pLP53-TLB was prepared as described in Example 4C.
D. Ligation and Transformation The DNA prepared in Example 5B was ligated with the DNA of Example 5C in substantial accordance with the method of Example 4D. The ligation mixture was used to transform *Escherichia coli* K12 AG1 cells by the method described in Example 1D. The transformants were selected by overnight growth on TY agar plates containing 100 µg/ml of ampicillin. Plasmid DNA was isolated from the ampicillin resistant clones by the DNA isolation procedure of Example 1E. These DNA samples were screened by restriction enzyme analysis for the desired plasmid, pTLB-t6E. A restriction site and function map of pTLB-t6E is shown in FIG. 11.

EXAMPLE 6

Construction of Plasmid pGT-t6D-d

A. Preparation of the 3862 Base Pair AatII-XmaI Restriction Fragment of Plasmid pmt6-hd Twenty µg of pmt6-hd (prepared in Example 2) was digested to completion with 10 µl (20 units) of AatII in a 150 µl reaction volume containing 10 mM Tris-HCl (pH 7.5), 50 mM KCl, 10 mM MgCl$_2$ and 1 mM DTT. The sample was incubated at 37° C. for 3 hours. Following incubation, the sample was purified and collected by ethanol precipitation and resuspended in 210 µl of water.

The above DNA was digested to completion with XmaI as follows. Twenty-five µl of 10× BRL Core buffer (500 mM Tris-HCl (pH 8.0), 100 mM MgCl$_2$ and 500 mM NaCl) and 15 µl of XmaI (15 units) were added to the sample. The sample was mixed and then incubated at 37° C. for 16 hours. Following incubation, the sample was purified, collected by ethanol precipitation and resuspended in 210 µl of water.

The above DNA was further digested with MstII to allow separation of the desired 3862 base pair AatII-BglII restriction fragment from other digestion products upon gel electrophoresis. Twenty-five µl of 10× buffer (100 mM MstII Tris-HCl (pH 7.5), 1.5M NaCl, 10 mM MgCl$_2$ and 2 mM 2-mercaptoethanol) and 15 µl of MstII (60 units) were added to the sample. The sample was mixed and then incubated at 37° C. for 2 hours. Following incubation the 3862 base pair AatII-BglII restriction fragment was isolated by preparative gel electrophoresis.

Figure 12:
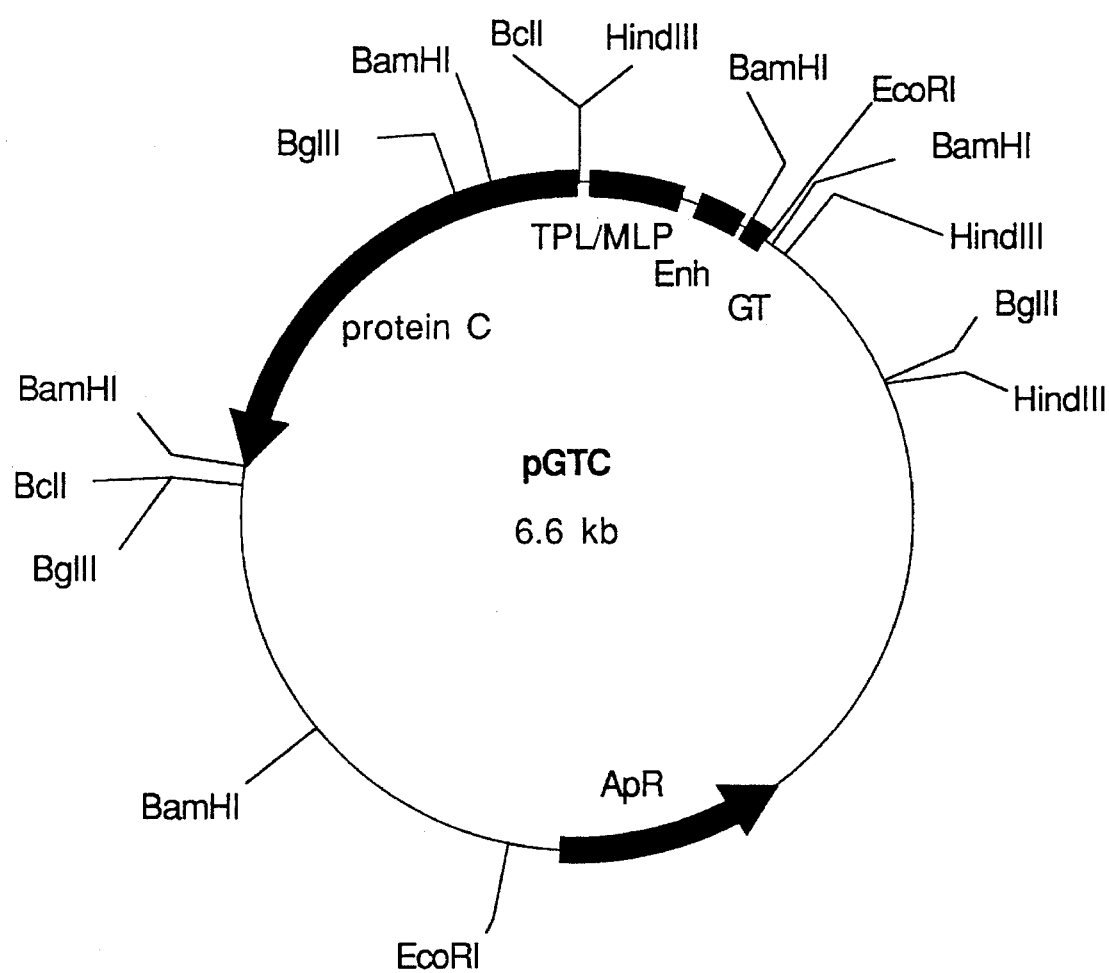
FIG. 12 is a restriction and function map of pGTC.

B. Preparation of the 3629 Base Pair BclI-AatII Restriction Fragment of Plasmid pGTC The plasmid pGTC can be conventionally isolated from *Escherichia coli* K12 AG1/pGTC, a culture deposited on Jan. 18, 1990 and made part of the permanent stock culture collection of the Northern Regional Research Center (NRRL), Agricultural Research Service, U.S. Department of Agriculture, Peoria, Ill. 61604, under accession number NRRL B-18593. A restriction site and function map of pGTC is shown in FIG. 12.

The plasmid pGTC was transformed into the dam- cell line *Escherichia coli* K12 GM48 as described in Example 1D. A dam- host cell is used because the recognition site for the restriction enzyme BclI (used below to digest plasmid pGTC) is partially modified by most *E. coli* strains. To digest DNA isolated from *E. coli* with BclI, it is necessary to use an *E. coli* strain deficient in adenine methylase (dam-). *E. coli* K12 GM48 is available from the NRRL under accession number NRRL B-15725. Other dam- cell lines may also be used. Plasmid DNA was isolated from these transformants as described in Example 1E.

Twenty-five µg of pGTC were digested to completion with 20 µl (40 units) of AatII in a 200 µl reaction volume containing 10 mM Tris-HCl (pH 7.5), 50 mM KCl, 10 mM MgCl$_2$ and 1 mM DTT. The sample was incubated at 37° C. for 3 hours. Following incubation, 30 µl of 10× Core buffer, 60 µl of water and 10 µl (100 units) of BclI were added to the sample. The sample was incubated at 37° C. for 3 hours. Following incubation the 3629 base pair AatII-BclI restriction fragment was isolated by preparative gel electrophoresis.

C. Preparation of the 1121 Base Pair XmaI-BamHI Restriction Fragment of Plasmid pTLB-t6D Twenty-five µg of pTLB-t6D (prepared in Example 4) was digested to completion in a reaction containing 20 µl (20 units) of XmaI, 5 µl of BamHI (50 units), 20 µl of 10× Core buffer (500 mM Tris-HCl (pH 8.0), 100 mM MgCl$_2$ and 500 mM NaCl) and 80 µl of water. The samples were incubated at 37° C. for 2 hours. Following incubation, the 1121 base pair BamHI-XmaI restriction fragment was isolated from each sample by preparative gel electrophoresis.

D. Ligation and Transformation

Figure 13:
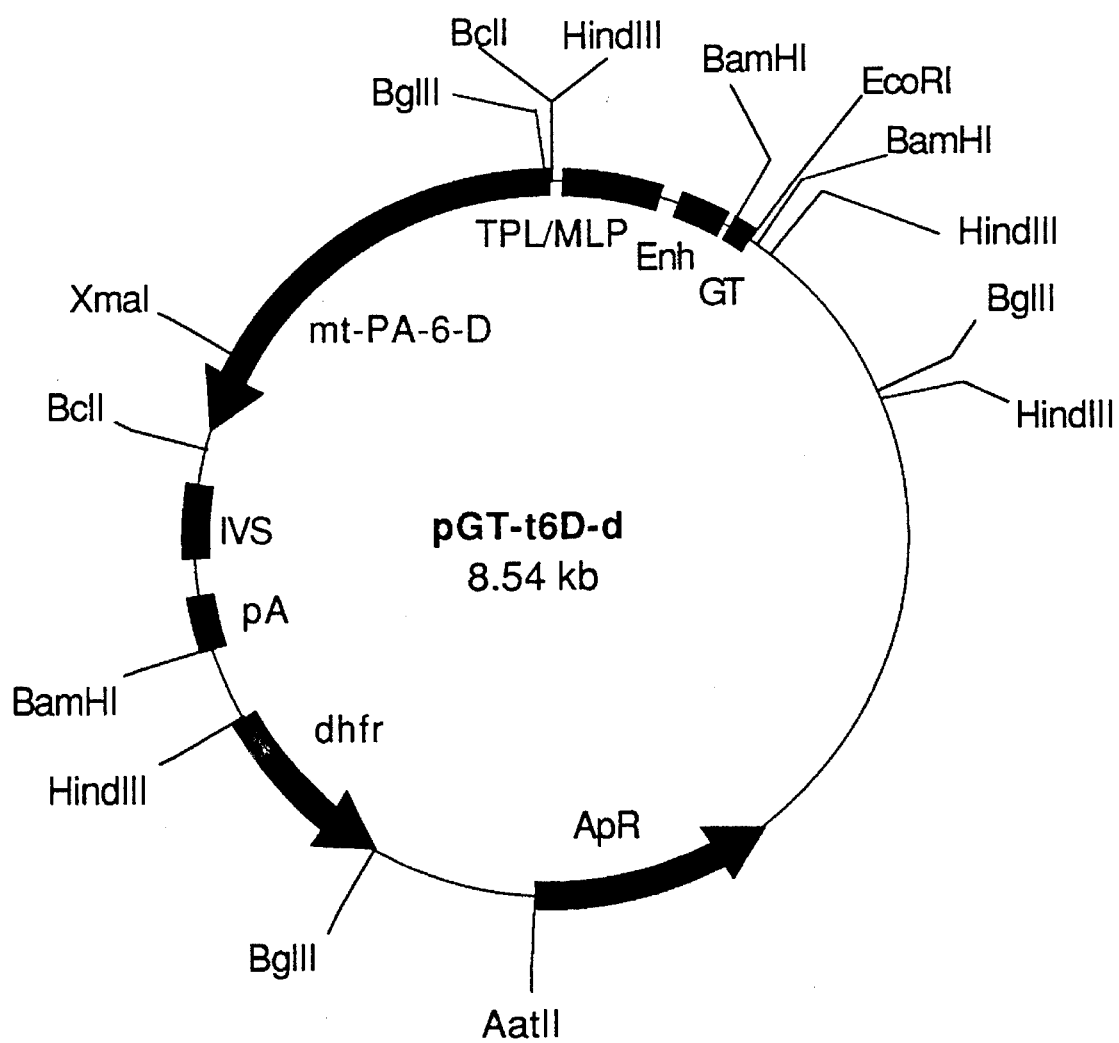
FIG. 13 is a restriction and function map of pGT-t6D-d.

One µl (0.02 µg) of the DNA prepared in Example 6A was ligated with one µl (0.02 µg) of the DNA from Example 6B and one µl (0.02 µg) of the DNA from Example 6C using T4 DNA ligase under the conditions described in Example 1C. A portion of the ligation mixture was used to transform *Escherichia coli* K12 AG1 cells as described in Example 1D. The ampicillin resistant transformants were selected, plasmid DNA was isolated from these resistant clones, and the desired plasmid, pGT-t6D-d, was identified by restriction enzyme analysis. A restriction site and function map of pGT-t6D-d is shown in FIG. 13.

EXAMPLE 7

Construction of Plasmid pGT-t6E-d

A. Preparation of the 3862 Base Pair AatII-XmaI Restriction Fragment of Plasmid pmt6-hd The 3865 base pair AatII-XmaI restriction fragment of plasmid pmt6-hd was prepared as described in Example 6A.

B. Preparation of the 3629 Base Pair BclI-AatII Restriction Fragment of Plasmid pGTC The 3629 base pair BclI-AatII restriction fragment of plasmid pGTC was prepared as described in Example 6B.

C. Preparation of the 1121 Base Pair XmaI-BglII Restriction Fragment of Plasmid pTLB-t6E The 1121 base pair XmaI-BglII restriction fragment of plasmid pTLB-t6E was prepared in accordance with the methods of Example 6C, however, the DNA of plasmic pTLB-t6E was substituted for that of plasmid pTLB-t6D.

D. Ligation and Transformation

Figure 14:
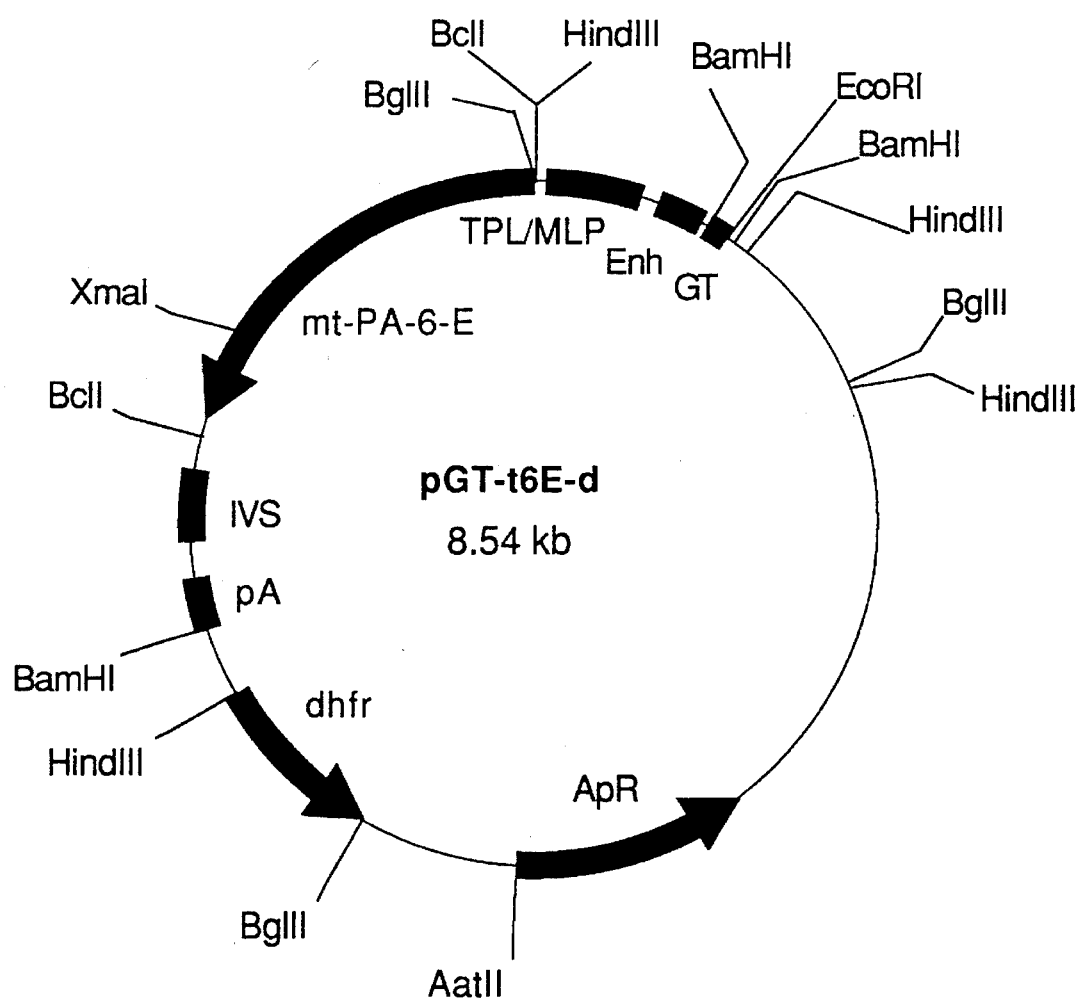
FIG. 14 is a restriction and function map of pGT-t6E-d.

One µl (0.02 µg) of the DNA prepared in Example 7A was ligated with one µl (0.02 µg) of the DNA from Example 7B and one µl (0.02 µg) of the DNA from Example 7C with T4 DNA ligase under the conditions described in Example 1C. A portion of the ligation mixture was used to transform *Escherichia coli* K12 AG1 cells as described in Example 1D. The ampicillin resistant transformants were selected, plasmid DNA was isolated from these resistant clones, and the desired plasmid, pGT-t6E-d, was identified by restriction enzyme analysis. A restriction site and function map of pGT-t6E-d is shown in FIG. 14.

EXAMPLE 8

Construction of Plasmid M13-ntPA

A. Preparation of the 1894 Base Pair BamHI Restriction Fragment of Plasmid pTPA603.

One hundred µg of plasmid pTPA603 (prepared in Example 2) was digested to completion with 100 units of BamHI in accordance with the methods of Example 3A. The 1894 base pair BamHI restriction fragment corresponding to the t-PA coding sequence was isolated in accordance with procedure of Example 3A and resuspended in 50 µl of water.

B. Preparation of BamHI Digested M13mp18 Vector.

One-half µg of M13mp18 replicative form DNA was linearized with BamHI in a reaction volume of 20 µl under the conditions described in Example 3A. Upon completion of the incubation of the sample, the reaction volume was increased to 100 µl and the sample was extracted with an equal volume of phenol:chloroform (1:1), followed by extraction with an equal volume of chloroform:isoamyl alcohol (24:1). The organic phases were back extracted with 100 µl TE buffer, aqueous phases were combined, precipitated with ethanol and suspended in 10 µl of dH2O.

C. Ligation and Transformation

One µl (0.01 µg) of the DNA prepared in Example 8B was ligated with two µl (0.05 µg) of the DNA prepared in Example 8A under the conditions described in Example 3C. Following ligation, a portion of the ligation mixture was used to transform *Escherichia coli* K12 AG1 cells as described in Example 1D. The transformants were selected as described in Example 3D and plasmid DNA was isolated from the transformants as described in Example 1E. The ligation reaction results in plasmids of two orientations. A plasmid which contained the DNA fragment of Example 8A in the proper orientation was identified by restriction analysis. The desired plasmid is called M13-ntPA.

EXAMPLE 9

Construction of pTLB-t9-d

A. Site-Specific Mutagenesis of Plasmid M13-ntPA

Oligonucleotide site specific mutagenesis was performed on plasmid M13-ntPA in substantial accordance with the procedures of Example 4A. Plasmid M13-ntPA was mutated in two steps. The first round of mutagenesis deleted exons 4 and 5 (corresponding to the F and GF domains). Thus, this new t-PA molecule made in the first round of mutagenesis contained the domains K1-K2-SP. The plasmid containing this derivative was called plasmid M13-tPA8. The mutagenic oligonucleotide used for the deletion of exons 4 and 5 had the sequence (SEQ. ID. NO: 27):

5'-GAGCCAGATC TTACCAAGAT ACCAGGGCCA CGTGC-TAC-3'.

For the second round of mutagenesis, plasmid M13-tPA8 was mutated to delete exons 7 and 8 forming plasmid M13-tPA9. Plasmid M13-tPA9 contains the new t-PA molecule KH-SP, where KH is the hybrid kringle comprised of the first exon from K1 and the second exon of K2. The mutagenic oligonucleotide used for the deletion of exons 7 and 8 had the sequence (SEQ. ID. NO: 28):

5'-GGGGAACCAC AACTACTGCA GGAATCCTGA TGGGGAT-GCC AAGCCC-3'.

After each round of mutagenesis, the mutated DNA was analyzed by DNA sequencing to confirm the success of the mutagenesis procedure. The final plasmid resulting from the two rounds of mutagenesis is M13-tPA9. The t-PA derivative encoded by this plasmid was called mt-PA9. The plasmid was grown up following a standard protocol for the propagation of M13 based vectors as described by Maniatis et al., supra.

B. Preparation of the 1010 bp XmaI-BglII mtPA9 fragment of M13-tPA9

Fifty μg of M13-tPA9 was digested with XmaI and BglII is accordance with the procedure of Example 4B. The 1010 base pair fragment corresponding to mt-PA9 was isolated by preparative gel electrophoresis and purified as described above.

C. Ligation for Plasmid pTLB-tPA9

Figure 15:
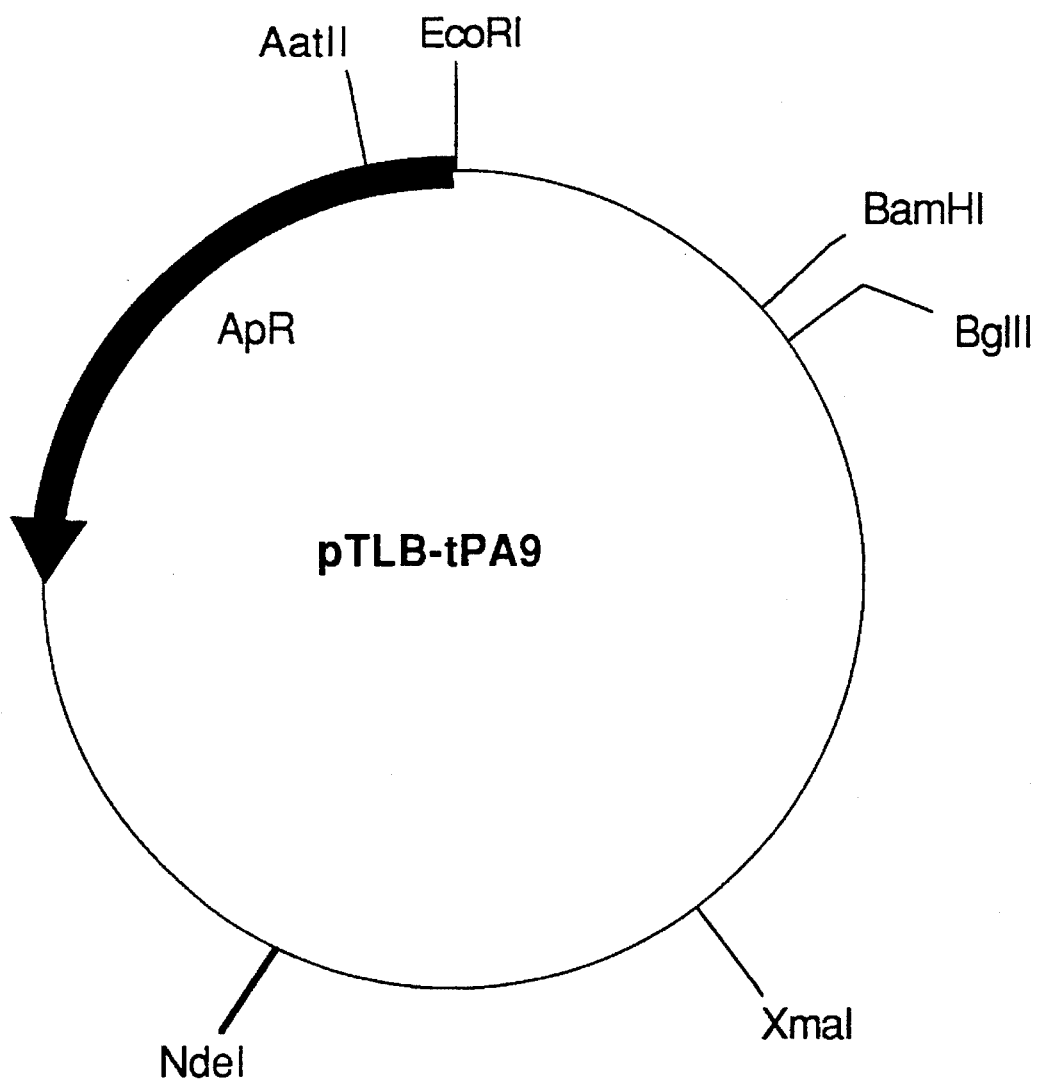
FIG. 15 is a restriction and function map of pTLB-tPA9.

About 0.05 μg of the 1010 bp DNA fragment prepared in Example 9B was ligated with about 0.01 μg of the DNA prepared in Example 4C in accordance with the methods of Example 3C. Following ligation, a portion of the ligation mixture was used to transform Escherichia coli K12 AG1 cells as described in Example 1D. The transformants were selected as described in Example 3D and plasmid DNA was isolated from the transformants as described in Example 1E. The resulting plasmid is called pTLB-tPA9. A restriction site and function map of plasmid pTLB-tPA9 is presented in FIG. 15.

EXAMPLE 10

Construction of pGT-BtPA9-d

A. Preparation of 1135 Base Pair XmaI-BamHI fragment of pTLB-tPA9

About 40 μg of pTLB-tPA9 was digested with XmaI-BamHI in a reaction volume of 100 μl in accordance with the method of Example 6C. The 1135 base pair XmaI-BamHI restriction fragment corresponding to the t-PA derivative mt-PA9 was isolated by preparative gel electrophoresis and purified as described above.

B. Ligation for pGT-BtPA9-d

Figure 16:
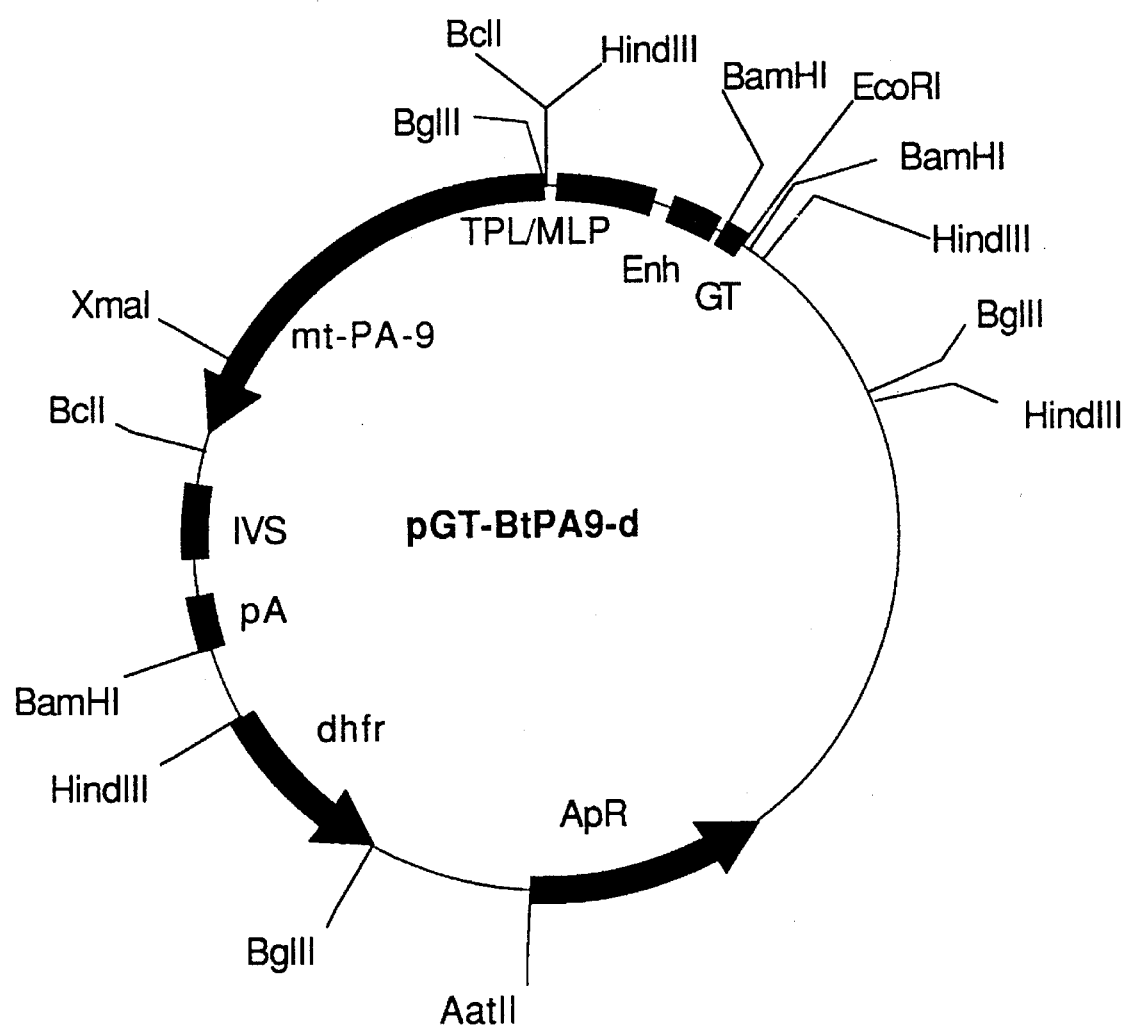
FIG. 16 is a restriction and function map of pGT-BtPA9-d.

About 0.02 μg of the DNA prepared in Example 10A, about 0.02 μg of the DNA prepared in Example 6A, and about 0.02 μg of the DNA prepared in Example 6B were ligated in accordance with the method of Example 1C. A portion of the ligation mixture was used to transform Escherichia coli K12 AG1 cells as described in Example 1D. The transformants were selected as described in Example 3D and plasmid DNA was isolated from the transformants as described in Example 1E. The resulting plasmid is called pGT-BtPA9-d. A restriction site and function map of plasmid pGT-BtPA9-d is presented in FIG. 16.

EXAMPLE 11

Transformation and Culturing

A. Transformation of AV12-664 Cells

The transformation procedure described below refers to AV12-664 cells as the host cell line; however, the procedure is generally applicable to most eucaryotic cell lines. AV12-664 cells are obtained from the ATCC under the accession number CRL 9595 in a 25 mm$^2$ flask containing a confluent monolayer of about $5.5 \times 10^6$ cells in Eagle's Minimum Essential Medium with 10% heat-inactivated horse serum. The flask is incubated at 37° C.; medium is changed twice weekly. The cells are subcultured by removing the medium, rinsing with Hank's Balanced Salts solution (Gibco, 3175 Staley Road, Grand Island, N.Y. 14072), adding 0.25% trypsin for 1–2 minutes, rinsing with fresh medium, aspirating, and dispensing into new flasks at a subcultivation ratio of 1:5 or 1:10.

One day prior to transformation, cells are seeded at $0.7 \times 10^6$ cells per 100 mm or 55 cm$^2$ dish. The medium is changed 4 hours prior to transformation. Sterile, ethanol-precipitated plasmid DNA dissolved in H$_2$O is used to prepare a 2× DNA-CaCl$_2$ solution containing 20 μg/ml DNA and 250 mM CaCl$_2$. 2× HBS is prepared containing 280 mM NaCl, 50 mM Hepes (N-2-Hydroxyethylpiperazine-N'-2-ethanesulfonic acid), and 1.5 mM sodium phosphate, with the pH adjusted to 7.05–7.15. The 2× DNA-CaCl$_2$ solution is added dropwise to an equal volume of sterile 2× HBS with a one ml sterile plastic pipette with a cotton plug while air is slowly bubbled through the solution. The calcium-phosphate-DNA precipitate is allowed to form without further agitation for 30–45 minutes at room temperature.

The precipitate is then mixed by gentle pipetting with a plastic pipette, and 0.5 ml (per plate) of precipitate is added directly to the 10 ml of growth medium that covers the recipient cells. After 4 hours of incubation at 37° C., the medium is replaced with DMEM containing 10% fetal bovine serum and the cells are allowed to incubate for an additional 72 hours before providing selective pressure. For plasmids that do not comprise a selectable marker that functions in eucaryotic cells, the transformation procedure utilizes a mixture of plasmids: the expression vector of the invention but lacking a selectable marker; and an expression vector that comprises a selectable marker that functions in eucaryotic cells. This cotransformation technique allows for the identification of cells that comprise both of the transforming plasmids by isolating colonies that grow in the presence of the selective pressure and assaying for the useful protein.

For cells transfected with plasmids containing the hygromycin resistance-conferring gene, hygromycin is added to the growth medium to a final concentration of about 200 to 400 μg/ml. AV12-664 cells can also be directly selected with methotrexate (200–500 nM) when transformed with a vector containing the murine dhfr gene. The cells are then incubated at 37° C. for 2–4 weeks with medium changes at 3 to 4 day intervals. The resulting hygromycin-resistant or methotrexate resistant colonies are transferred to individual culture flasks for characterization.

EXAMPLE 12

Isolation and Purification

The tissue plasminogen activator molecules of the present invention are isolated from the culture medium by methods well known in the art such as those described by Burck et al., supra. The two forms of mt-PA6 can be separated by affinity chromatography in substantial accordance with the method of Einarsson et al., 1985, *Biochim. Biophys. Acta* 830:1–10, and Rijken et al., 1985, *Thromb. and haemostas.* 54(4), 788–791. Preferably, mt-PA6-V is isolated by preparative hydrophobic interaction chromatography using a TSK phenyl-5PW column (20 mm ID+150 mm long) as follows. Mobile Phase A was 1M potassium phosphate, 2M urea, 0.02% sodium azide, pH 8.5. Mobile Phase B was the same as Mobile Phase A except that the potassium phosphate concentration was 0.02M. The plasminogen activator was applied to the column in 50% Mobile Phase A/50% Mobile Phase B. The separation was performed using an initial eluent composition of 20% Mobile Phase B. After 15 minutes the eluent composition was increased to 50% Mobile Phase B, and then to Mobile Phase B. The fractions were acidified to pH 3.0 with HCl, dialyzed against 0.001M HCl/0.001% Tween 80, and lyopholized. The fractions were stored at 20° C. The t-PA derivatives can also be isolated by use of a PAM-1 Sepharose column (available from American Diagnostica, 222 Railroad Ave. P.O. Box 1165 Greenwich Conn.).

EXAMPLE 13

Analysis

A. SDS-PAGE Analysis

The purified t-PA derivative samples were analyzed by SDS-PAGE. This analysis indicated that the derivative t-PA molecules produced by AV12-664/pGT-t6D-d, AV12-664/pGT-t6E-d and AV12-664/pGT-BtPA9-d were of the same molecular weight as mt-PA6-V. This indicated that the host cells containing the recombinant DNA vectors of the present invention produced a homogeneous population of diglycosylated t-PA derivative molecules.

B. Activation of Lysine (Lys)-Plasminogen and Glutamic Acid (Glu)-Plasminogen

A comparison of the ability of the single chain and two chain forms of the mt-PA6-V derivatives to activate Lys- or Glu-plasminogen was also performed in the presence of fibrin stimulator. The method used was that described by Ranby et al., 1982, *Thrombo. Res.* 27:743–749. Single chain forms of the t-PA derivatives were converted to the two chain form by incubation of a 1 μM solution of the t-PA derivative in 0.1M NaCl, 0.1 mg/ml BSA, 20 mM Tris HCl (pH 7.4) 0.01% Tween 80 and 1.5 nM human plasmin (Boehringer Mannheim) at 37° C. for 1 hour. Progress of the reaction was monitored with the chromgenic substrate S2288 (H-D-Isoleucyl-L-prolyl-L-arginine-p-nitroaniline-dihydrochloride; KabiVitrum, Stockholm, Sweden), and the reaction was stopped by addition of aprotinin (Sigma). A higher ratio of Lys:Glu plasminogen activation indicates potentially higher in vivo fibrin clot specificity. The results, shown in Table 1, indicate that the t-PA derivatives of the present invention are at least as fibrin clot specific as mt-PA6-V. In fact, the mt-PA6-D derivative demonstrated an increased ability to activate Lys-plasminogen in the presence of fibrin indicating that this derivative is potentially more fibrin clot specific in vivo than mt-PA6-V. The increased plasminogenolytic activity of all the diglycosylated forms towards Lys-plasminogen versus Glu-plasminogen suggests an improved clot specificity of these molecules.

TABLE 1

Ratio of the Rates of Glu to Lys-Plasminogen Activation in the Presence of Fibrin Stimulator

|  | single chain Lys/Glu | two-chain Lys/Glu |
| --- | --- | --- |
| mt-PA6-D | 3.3 | 2.6 |
| mt-PA6-E | 2.0 | 1.5 |
| mt-PA6-V | 1.4 | 1.4 |
| mt-PA6-P | 1.0 | 1.2 |
| mt-PA9 | 2.0 | 1.8 |

C. Plasmin Sensitivity

The plasmin sensitivities of the t-PA derivatives were measured in a reaction mixture that contained 120–200 nM of the t-PA derivative in a buffer consisting essentially of 0.15M NaCl; 0.1 μg/ml BSA; 50 mM Tris-HCl (pH 7.4) and 0.01% Tween 80, and 11 nM human plasmin (Boehringer Mannheim). Aliquots of this reaction mixture were removed at various time points to microtiter wells that contained 200 KIU aprotinin (Sigma Chemical Co., St. Louis Mo. 63178). The chromogenic substrate S2288 (Kabi Vitrum) was added to the samples in order to monitor the progress of the reaction at each time point. Data from plasmin digests known to generate 100% conversion to the two-chain form of t-PA were used to calculate percent conversion to two chain form for each derivative. The results indicate that mt-PA6-D mt-PA6-E are more resistant to plasmin than mt-PA6-P.

D. Enzymatic Activity

Amidolytic and Plasminogenolytic activities of the t-PA derivatives are shown in Table 2. Amidolytic activities (AU/mg) were determined by use of the chromogenic substrate S2288 as described in Example 13C.

Plasminogen activities were measured using the Spectrolyse Tissue Plasminogen Activator Activity and Inhibitor Assay kit (American Diagnostica, 222 Railroad Ave., P.O. Box 1165, Greenwich Conn., Catalog #452). The reactions were monitored by a ThermoMax™ plate reader (Molecular Devices, Palo Alto Calif.) and SoftMax™ software.

Table 2 shows the ratio of amidolytic to plasminogenolytic activities of the t-PA derivatives as compared to mt-PA6-P. One unit (u) is defined as the amount of plasminogen activator required to release 1 μmole of p-nitroanilide in 1 minute at 25° C. at 405 nm using an extinction coefficient for p-nitroanilide of 9620 $M^{-1}$ $cm^{-1}$. The higher ratios of activity toward plasminogen with the mt-PA6-D derivative indicate an increase in substrate specificity.

TABLE 2

Enzymatic Activities of Derivative Plasminogen Activators

|  | AU/mg | PAU/mg | PAU/AU |
| --- | --- | --- | --- |
| mt-PA6-D |  |  |  |
| single chain | 0.59 | 189 | 320 (4.6) |
| two chain | 3.51 | 784 | 224 (2.4) |
| mt-PA6-E |  |  |  |
| single chain | 0.93 | 59 | 63 (0.91) |

TABLE 2-continued

Enzymatic Activities of Derivative Plasminogen Activators

|  | AU/mg | PAU/mg | PAU/AU |
|---|---|---|---|
| two chain mt-PA6-P | 5.25 | 563 | 107 (1.1) |
| single chain mt-PA6-V | 1.26 | 87 | 69 (1) |
| two chain mt-PA6-V | 5.69 | 539 | 95 (1) |
| single chain mt-PA9 | 1.50 | 56 | 38 (0.54) |
| two chain mt-PA9 | 7.17 | 451 | 58 (0.61) |
| single chain t-PA | 1.12 | 50 | 45 (0.65) |
| two chain t-PA | 6.69 | 589 | 88 (0.93) |
| single chain | 1.5 | n.d. | n.d. |
| two chain | 5.99 | n.d. | n.d. |

E. Clot Lysis Activity

The ability of the t-PA derivatives of the present invention to lyse clots was determined using a modification of the microtiter plate method described by Beebe et al., 1987, *Thrombosis Res.* 47:123–128. Fifty μl of assayed human reference plasma (Helena Laboratories) was mixed with 50 μl of APTT reagent (Helena Laboratories) and 30 μl of various concentrations of the t-PA derivatives in a buffer consisting of 0.001N HCl, 0.011% Tween 80, 50 mM Tris (pH 8.0), and 250 mM NaCl. The mixture was incubated for 5 minutes at 37° C. Clot formation was initiated by addition of 25 μl of 100 mM $CaCl_2$. The formation and subsequent dissolution of the clot were monitored by a ThermoMax™ plate reader (Molecular Devices) and SoftMax™ software. Rates of clot lysis were determined from the slopes of the decay curves and correlated (r=0.992) with the time of 50% clot lysis.

As shown in Table 3, the rates of clot lysis for the t-PA derivatives were lower that t-PA at lower levels of enzyme. However, at concentrations approximating therapeutic blood levels, high rates of clot lysis were observed with each derivative.

TABLE 3

Rate of Clot Lysis (mOD/min)

| Concentration (nM) | 11 | 23 | 45 | 114 | 227 |
|---|---|---|---|---|---|
| t-PA | 7.1 | 9.0 | 12.3 | 14.0 | 14.5 |
| mt-PA6-P | 0 | 2.5 | 6.9 | 12.5 | 12.8 |
| mt-PA6-V | 0 | 1 | 3.9 | 11.0 | 12.8 |
| mt-PA-9 | 0 | 0 | 1.0 | 6.0 | 9.5 |
| mt-PA6-D | 0 | 3.5 | 4.5 | 8.3 | 11.2 |
| mt-PA6-E | 0 | 0 | 4.5 | 9.1 | 12.0 |

F. Effect of the t-PA Derivatives on Plasma Fibrinogen Levels

To determine the effect of the t-PA derivatives on plasma fibrinogen, 5 μl of an 80 μg/ml solution of each t-PA derivative in 0.001N HCl, 0.011% Tween 80, 50 mM Tris (pH 8.0), and 250 mM NaCl plus 25 μl of phosphate buffered saline were incubated with 50 μl of assayed reference plasma (Helena Laboratories) for various times. The level of plasminogen in the plasma was determined by the change in clotting time upon addition of 10 μl of 3 units/ml of bovine thrombin (Miles Laboratories) essentially by the method of Clauss, 1957, *Acta Haematol.* 17:237. The data is shown in Table 4 and is reported as the amount of fibrinogen degraded in the plasma sample. The results of this analysis show that the level of fibrinogen remaining at all times assayed was higher for mt-PA6D and mt-PA6-E. This indicates that these derivatives may be more fibrinogen sparing, thus resulting in reduced bleeding liability to the treated patient.

TABLE 4

Fibrinogen Depleted (mg/dl)

| Time (min.) | 122 | 207 | 272 |
|---|---|---|---|
| t-PA | 12 | 31 | 45 |
| mt-PA6-P | 2 | 33 | 35 |
| mt-PA6-V | 3 | 21 | 35 |
| mt-PA9 | 5 | 9 | 28 |
| mt-PA6-D | 5 | 10 | 16 |
| mt-PA6-E | 7 | 4 | 5 |

We claim:

1. A human tissue-plasminogen activator (t-PA) derivative lacking Finger, Growth Factor, and Kringle 1 domains which comprises a Kringle 2 domain that is monoglycosylated at an amino acid residue equivalent to amino acid residue number 218 of native human t-PA.

2. A human t-PA derivative lacking Finger, Growth Factor, and Kringle 1 domains which comprises a Kringle 2 domain that is monoglycosylated at amino acid residue number 47.

3. The t-PA derivative of claim 2 which is mt-PA6-E (SEQ. ID. NO: 6).

4. A human t-PA derivative lacking Finger and Growth Factor domains and having a chimeric Kringle 1 and 2 domains which is mt-PA9 (SEQ. ID NO: 8).

5. A pharmaceutical composition comprising the t-PA derivative of claim 1 in combination with a pharmaceutically acceptable carrier, diluent, or excipient.

6. A pharmaceutical composition comprising the t-PA derivative of claim 2 in combination with a pharmaceutically acceptable carrier, diluent, or excipient.

7. A pharmaceutical composition comprising the t-PA derivative of claim 3 in combination with a pharmaceutically acceptable carrier, diluent, or excipient.

8. A pharmaceutical composition comprising the t-PA derivative of claim 4 in combination with a pharmaceutically acceptable carrier, diluent, or excipient.

\* \* \* \* \*